US009157842B1

(12) United States Patent
Ancona et al.

(10) Patent No.: US 9,157,842 B1
(45) Date of Patent: *Oct. 13, 2015

(54) MOLECULAR CONCENTRATOR BASED ON THERMAL RATCHETING

(71) Applicants: Mario Ancona, Alexandria, VA (US);
Arthur W. Snow, Alexandria, VA (US);
F. Keith Perkins, Alexandria, VA (US)

(72) Inventors: Mario Ancona, Alexandria, VA (US);
Arthur W. Snow, Alexandria, VA (US);
F. Keith Perkins, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/614,481

(22) Filed: Feb. 5, 2015

Related U.S. Application Data

(63) Continuation-in-part of application No. 14/279,394, filed on May 16, 2014, now Pat. No. 8,986,615.

(51) Int. Cl.
G01N 1/40 (2006.01)
B01D 53/04 (2006.01)
G01N 30/38 (2006.01)

(52) U.S. Cl.
CPC ............ *G01N 1/405* (2013.01); *B01D 53/0462* (2013.01); *G01N 30/38* (2013.01)

(58) Field of Classification Search
CPC ................ G01N 2030/008; G01N 2030/0085; G01N 2030/0075; G01N 2001/4022; G01N 1/405; B01D 53/0462
USPC .............................. 73/23.41; 422/88; 436/178
See application file for complete search history.

(56) References Cited

U.S. PATENT DOCUMENTS

| 6,345,545 | B1 * | 2/2002 | Linker et al. ............... 73/863.23 |
| 6,393,894 | B1 * | 5/2002 | Bonne et al. .................. 73/23.2 |
| 6,792,794 | B2 * | 9/2004 | Bonne et al. ................. 73/25.01 |
| 6,837,118 | B2 * | 1/2005 | Bonne et al. ............... 73/863.12 |
| 7,168,298 | B1 * | 1/2007 | Manginell et al. ........... 73/54.25 |
| 7,578,167 | B2 * | 8/2009 | Bonne et al. ................. 73/25.01 |
| 7,654,129 | B2 * | 2/2010 | Bonne et al. ................. 73/23.21 |
| 7,779,671 | B2 * | 8/2010 | Bonne .......................... 73/25.01 |
| 8,448,532 | B2 * | 5/2013 | Martin et al. .............. 73/863.12 |

(Continued)

OTHER PUBLICATIONS

P.E. Sheehan et al., "Detection Limits for Nanoscale Biosensors," Nano Letters, vol. 5, No. 4, pp. 803-807 (2005).

(Continued)

*Primary Examiner* — Peter Macchiarolo
*Assistant Examiner* — Nathaniel Kolb
(74) *Attorney, Agent, or Firm* — US Naval Research Laboratory; Joslyn Barritt

(57) ABSTRACT

A molecular concentrator comprising a thermal ratchet for driving molecules from one place to another. A plurality of linear, two-dimensional, and/or three-dimensional arrangements of heater structures are arranged on or suspended above a substrate. Each of the heater structures is configured to strongly sorb a vapor of interest when the heater structure is at room temperature and to rapidly desorb the vapor when the heater structure is at an elevated temperature. The vapor sorption of the individual heater structures is made selective by surface treatments, by monomolecular film depositions or by thicker absorbent polymer depositions. By selectively heating and cooling the heater structures, vapor molecules incident on the heater structures can be directed in a desired manner, e.g., from heater structures closest to a vapor-containing environment to a sensor.

35 Claims, 18 Drawing Sheets

(56) References Cited

U.S. PATENT DOCUMENTS

| | | | |
|---|---|---|---|
| 2004/0060346 A1* | 4/2004 | Bonne et al. | 73/61.44 |
| 2006/0228261 A1* | 10/2006 | Iwamoto et al. | 422/88 |
| 2007/0028670 A1* | 2/2007 | Bonne et al. | 73/31.05 |
| 2007/0274867 A1* | 11/2007 | Iwamoto et al. | 422/88 |
| 2008/0163674 A1* | 7/2008 | Bonne et al. | 73/31.05 |
| 2009/0084162 A1* | 4/2009 | Besnard et al. | 73/31.06 |
| 2009/0100906 A1* | 4/2009 | Bonne | 73/25.03 |
| 2010/0236341 A1* | 9/2010 | Martin et al. | 73/863.12 |
| 2010/0239436 A1* | 9/2010 | Bonne et al. | 417/207 |
| 2011/0247394 A1* | 10/2011 | McBrady | 73/23.41 |

OTHER PUBLICATIONS

I. Voiculescu, et al., "Microfabricated chemical preconcentrators for gas-phase microanalytical detection systems," Trends in Analytical Chemistry, vol. 27, No. 4, pp. 327-343 (2008).

W.A. Groves, et al., Analyzing organic vapors in exhaled breath using a surface acoustic wave sensor array with preconcentration: Selection and characterization of the preconcentrator adsorbent, Anal. Chim. Acta 371, 131-143 (1998).

I. Voiculescu, et al., "Micropreconcentrator for Enhanced Trace Detection of Explosives and Chemical Agents," IEEE Sensors J. 6, 1094-1104 (2006).

Q. Zhong et al., Characterization of a high-performance portable GC with a chemiresistor array detector, Analyst 134, 283-293 (2009).

M.D. Hsieh et al., "Limits of Recognition for Simple Vapor Mixtures Determined with a Microsensor Array," Anal. Chem. 76, 1885-1895 (2004).

B. Alfeeli et al., "MEMS-based multi-inlet/outlet preconcentrator coated by inkjet printing of polymer adsorbents," Sensors and Actuators B 133, 24-32 (2008).

R.E. Shaffer et al., "Multiway Analysis of Preconcentrator-Sampled Surface Acoustic Wave Chemical Sensor Array Data," Field Anal. Chem. Tech. 2, 179-192 (1998).

T. Nakamoto et al., "Odor-sensing system using preconcentrator with variable temperature," Sensors and Actuators B 69, 58-62 (2000).

C.E. Davis et al., "Enhanced detection of m-xylene using a preconcentrator with a chemiresistor sensor," Sensors and Actuators B 104, 207-216 (2005).

M.G. Ancona et al., "Scaling Properties of Gold Nanocluster Chemiresistor Sensors," IEEE Sensors Journal 6, 1403-1414 (2006).

M.G. Ancona, et al., "Analyte kinetics in a nanocluster-based chemiresistor: A case study," Sensors and Actuators B 177, 936-946 (2013).

B.H. Kear, et al. "Surface Treatments Using the Laser, Electron and Ion Beam Processing Methods," Metall. Treatises (J.K. Tien and J.F. Elliott, eds.), 1981, pp. 321-343.

M.C. Kim, et al. "Surface treatment of metals using an atmospheric pressure plasma jet and their surface characteristics," Surface and Coatings Technology, 2003, 174, 839.

A.W. Snow, et al., "Packing density of $HS(CH_2)_nCOOH$ self-assembled monolayers," Analyst 2011, 135, 4935.

A. Voelkel, "Inverse Gas-Chromatography—Characterization of Polymers, Fibers, Modified Silicas, and Surfactants," Cult. Rev. Anal. Chem. 1991, 22, 411-439.

G.M. Gross, et al., "Recent Advances in Instrumentation for Gas Chromatography," Curr. Anal. Chem. 2005, 1, 135-147.

A.W. Snow, et al., "Disordered nanomaterials for chemielectric vapor sensing," IEEE Sensors J. 15, 1301 (2015).

* cited by examiner

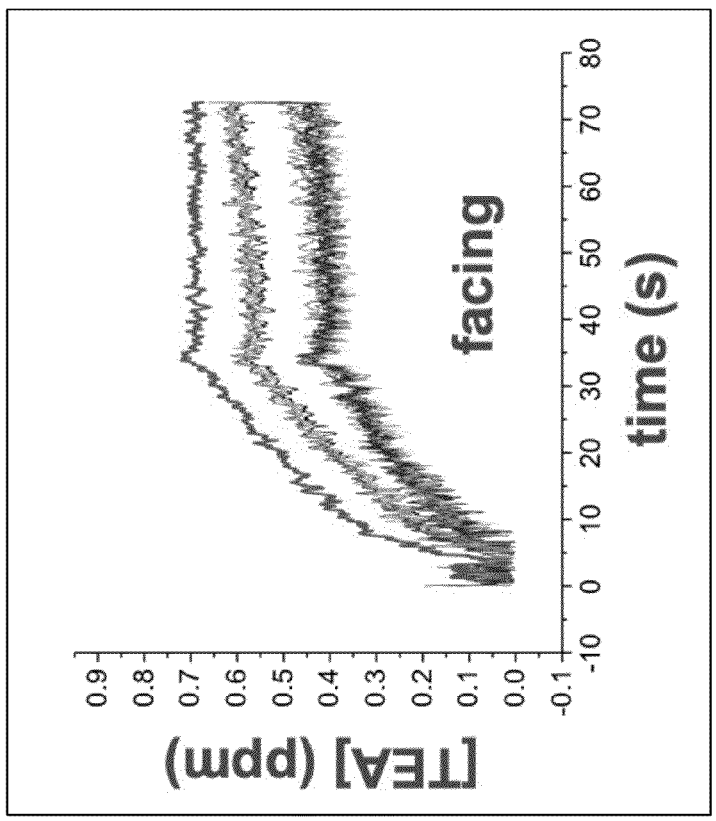
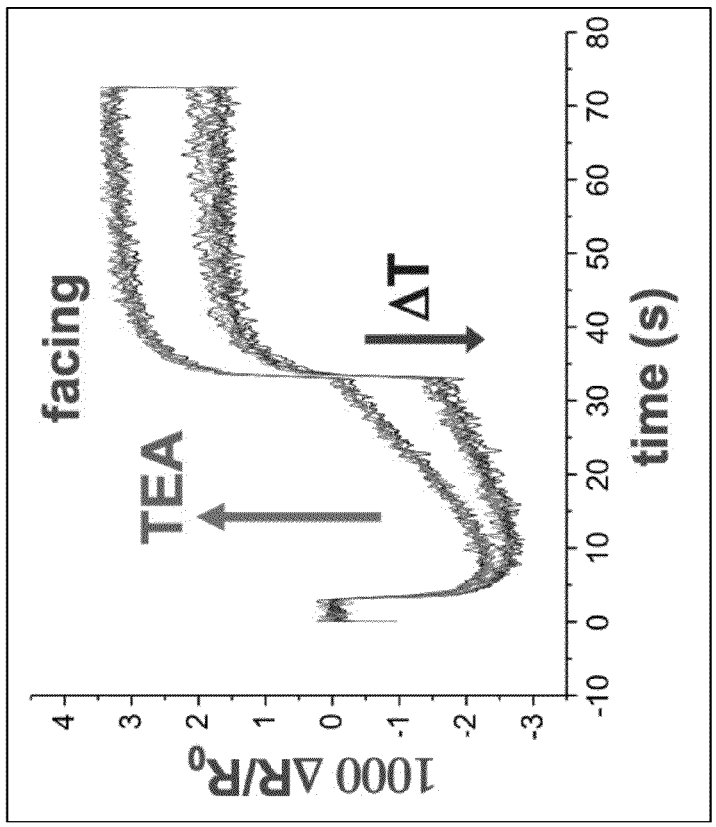
FIG. 10B
FIG. 10A

MOLECULAR CONCENTRATOR BASED ON THERMAL RATCHETING

CROSS-REFERENCE

This application is a Continuation-in-Part of, and claims the benefit of priority under 35 U.S.C. §120 based on, U.S. patent application Ser. No. 14/279,394 filed May 16, 2014, the entirety of which is hereby incorporated by reference into the present application.

TECHNICAL FIELD

The present invention relates to the detection of vapors, and particularly to the collection of trace levels of vapor analyte for delivery to a point sensor.

BACKGROUND

Detection of analytes as dilute vapors requires not only a capable sensor, but also an efficient means for collecting, concentrating, and delivering the vapor analytes from the environment to the sensor. The need for the latter functionality and its challenges when the vapor is at trace levels are referred to as the "sampling problem."

In general, the difficulties of sampling, for both aqueous and vapor sensing, stem from diffusion limits, and specifically from the time required for the vapor molecules to "find" the sensor. See, e.g., P. E. Sheehan et al., "Detection Limits for Nanoscale Biosensors," NANO LETTERS, Vol. 5, No. 4, pp. 803-807 (2005).

These difficulties are relatively independent of sensor size. Although a larger sensor is more easily "found," it requires more molecules to generate the same response (though larger sensors do generally benefit from a lower noise floor).

A well-known approach for enhancing sensitivity/selectivity at the cost of response time is to use a pre-concentrator that consists of a large area/volume of adsorbent material that can gather vapor molecules over time, and then with rapid heating, pump the desorbed and now concentrated vapor over the sensor. See I. Voiculescu, et al., "Microfabricated chemical preconcentrators for gas-phase microanalytical detection systems," *Trends in Analytical Chemistry*, Vol. 27, No. 4, pp. 327-343 (2008). Of particular relevance to vapor sensing are W. A. Groves, et al., "Analyzing organic vapors in exhaled breath using a surface acoustic wave sensor array with pre-concentration: Selection and characterization of the preconcentrator adsorbent, *Anal. Chim. Acta* 371, 131-143 (1998); I. Voiculescu, et al., "Micropreconcentrator for Enhanced Trace Detection of Explosives and Chemical Agents," *IEEE Sensors J.* 6, 1094-1104 (2006); Q. Zhong et al., "Characterization of a high-performance portable GC with a chemiresistor array detector, *Analyst* 134, 283-293 (2009); M. D. Hsieh et al., "Limits of Recognition for Simple Vapor Mixtures Determined with a Microsensor Array," *Anal. Chem.* 76, 1885-1895 (2004); B. Alfeeli et al., "MEMS-based multi-inlet/outlet preconcentrator coated by inkjet printing of polymer adsorbents," *Sensors and Actuators* B 133, 24-32 (2008); R. E. Shaffer et al., "Multiway Analysis of Preconcentrator-Sampled Surface Acoustic Wave Chemical Sensor Array Data," *Field Anal. Chem. Tech.* 2, 179-192 (1998); T. Nakamoto et al., "Odor-sensing system using preconcentrator with variable temperature," *Sensors and Actuators* B 69, 58-62 (2000); and C. E. Davis et al., "Enhanced detection of m-xylene using a preconcentrator with a chemiresistor sensor," *Sensors and Actuators* B 104, 207-216 (2005).

Although useful, the pre-concentrator scheme remains diffusion-limited, both in the initial collection from the ambient, and in the transfer from the pumped air stream to the sensor. For example, although it might seem that much could be gained by having a large ratio between the areas of the pre-concentrator and sensor, the bigger this ratio the faster the air stream velocity over the sensor must be and the less time there will be available for analyte to out-diffuse onto the sensor, and a fundamental diffusion limit still remains.

The key to overcoming the diffusion limit and enabling efficient collection, concentration, and delivery of analyte molecules to a sensor thus appears to involve having a way of moving the molecules by means other than a carrier gas such as air. As already noted, no artificial method, material, or apparatus currently exists for doing this and thereby for surmounting the diffusion limitation.

However, there are biological sensing systems that do achieve extraordinary levels of sensitivity and it is thought that an essential aspect is a method for molecular delivery. For example, the antennae of moths serve as means of collecting exceedingly sparse pheromone molecules from the environment (as emitted by distant females) and then delivering them (without a carrier gas) to a receptor for detection. As discussed in the next section, the invention disclosed herein provides for the first time an artificial means for accomplishing similar molecular transport, though by a mechanism different from that used biologically.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present invention provides an apparatus and method for transporting desired analyte molecules in a vapor from an environment containing the vapor to a sensor. The present invention can simultaneously concentrate the selected vapor analyte and separate it from among interferents so that it can be more easily detected and analyzed. This apparatus and method are therefore often referred to herein as a "molecular concentrator."

The basic mechanism or method of the molecular concentrator provided by the present invention can be described as a thermal ratchet for driving molecules from one place to another.

In accordance with the present invention, a plurality of heater wires are arranged on or suspended above a substrate. Each of the wires is configured to strongly sorb the vapor of interest at room temperature and to rapidly desorb it at an elevated temperature. By selectively heating one or more of the wires, a concentration of vapor molecules can be directed in a desired manner, e.g., from one wire to its neighbor or ultimately from the wires closest to the vapor-containing environment to a sensing device. In some embodiments, the surfaces of one or more of the wires may be bare metal, while in other embodiments they may have a selective coating that is constituted to sorb one or more specified vapors of interest more strongly than others.

In an exemplary embodiment, the thermal ratchet in accordance with the present invention can serve as a molecular concentrator. In such an embodiment, the heater wires can be configured as an array of concentric wires with a sensor at the center. The thermal ratchet mechanism is then used to drive analyte molecules from the periphery (adjacent to the environment) to the sensor where they can be detected and analyzed.

BRIEF DESCRIPTION OF THE DRAWINGS

FIGS. 10A and 10B are plots showing measured sensor characteristics for the facing sensor in response to (primary) emission of TEA from a heated wire in accordance with the present invention

DETAILED DESCRIPTION

Figure 1:
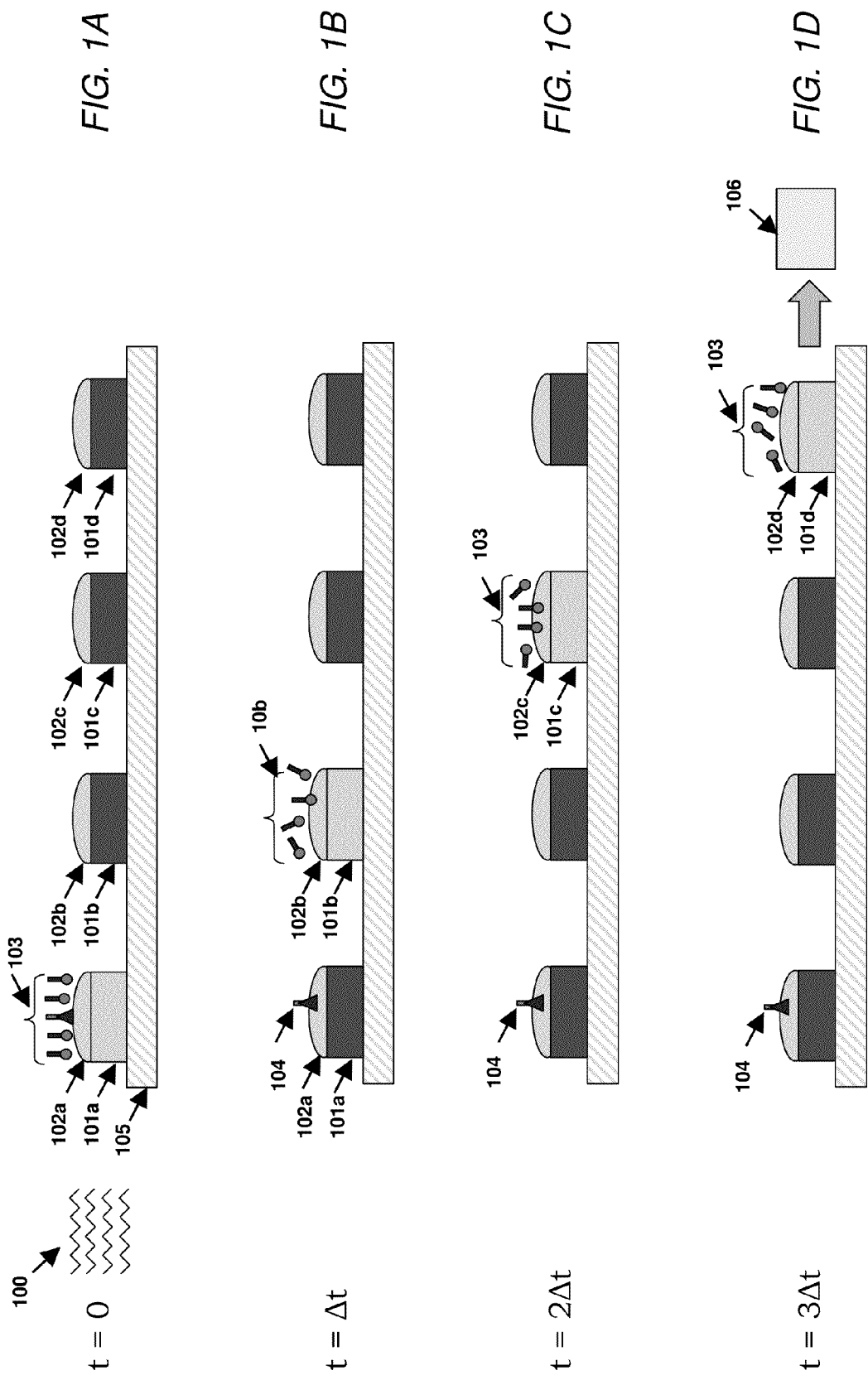
FIGS. 1A-1D are block diagrams illustrating the basic thermal ratcheting transfer mechanism by which the molecular concentrator of the present invention operates.

The aspects and features of the present invention summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

For example, although the present invention is described herein in the context of embodiments based on the use of an arrangement of heater wires, it may be possible to use other heater structures, materials, and/or geometries to accomplish the thermal ratcheting described herein. In addition, although the invention has been described as using coated heater structures, in some embodiments, appropriately configured uncoated structures made from materials that sorb and desorb vapor molecules as described may be also used. All such alternatives and other embodiments are deemed to be within the scope of the present invention.

The present invention provides an apparatus and method for transporting desired analyte molecules from an environment containing the vapor to a sensor. The present invention can simultaneously concentrate the selected vapor analyte and separate it from among interferents so that it can be more easily sensed and analyzed, and is therefore often referred to herein as a "molecular concentrator."

The basic mechanism or method of a molecular concentrator provided by the present invention can be described as a thermal ratchet for driving molecules from one place to another. The ratchet mechanism is instituted by heating a set of vapor-absorbing wires in proper sequence in order to drive the molecules in the direction perpendicular to the wires. The movement of the molecules from one wire to another occurs without the carrier gas that is required by conventional preconcentrator technologies and by gas chromatography.

FIGS. 1A-1D are block diagrams illustrating the basic mechanism of a molecular concentrator based on thermal ratcheting in accordance with the present invention. It should be noted that the particular sequencing of wire heating depicted in these FIGURES is just one possibility for achieving the desired analyte transfer, and one skilled in the art will readily appreciate that other predefined sequences of wire heating are also within the scope of the present disclosure.

In the exemplary embodiment illustrated in FIGS. 1A-1D, a thermally ratcheting molecular concentrator in accordance with the present invention comprises a plurality of parallel wires $101a$-$d$ (or equivalent heater structures), shown in cross-section in the FIGURE, arranged on (or, as described below, suspended above) a substrate 105. Each of the wires is coupled to a source of heat energy, and in some embodiments, are also coupled to a source of cooling energy, where, as described below, the heat and/or cooling energy can be selectively applied to one or more of the wires. In the exemplary embodiment shown in FIGS. 1A-1D, each of the wires has a coating $102a$-$d$ on the surface thereof, wherein the coating is an absorbent material that selectively sorbs the vapor of interest at room temperature and rapidly desorbs the vapor at an elevated temperature. The coated wires $101/102a$-$d$ have a low thermal mass and can be heated by applying the heat energy into the wire, e.g., through resistive heating produced by running a current through the wire, and can be cooled by removing the heat energy or, in some embodiments, by applying a cooling energy to the wire. When a wire is heated, the vapor of interest is desorbed from the surface of the wire, with the vapor then being resorbed on a neighboring wire which is at or below room temperature. In accordance with the present invention, by selectively applying and removing heat energy to the wires in a predefined sequence, it is possible to direct and focus vapor molecules incident on the wires a desired manner, e.g., from the wires closest to the vapor-containing environment to wires closest to a sensor.

Thus, at time t=0, as illustrated in FIG. 1A, vapor 100 is incident on a wire structure in which wire 101a is at room temperature while wires 101b, 101c, and 101d are at an elevated temperature. As illustrated in FIG. 1A, there is a strong sorption of the vapor (shown as vapor molecules 103) onto room-temperature wire 101a but not onto heated wires 101b, c, or d. Next, as depicted in FIG. 1B, at a time t=Δt, wire 101a is suddenly heated while wire 101b is rapidly cooled to room temperature (or below), with wires 101c and 101d remaining heated. The wires are thermally well isolated one from another, so that a heating or cooling of one wire does not heat or cool a neighboring wire, aside from gas or vapor conduction. Thus, when wire 101a is cooled, (and with no other adsorbent surfaces nearby), most of the vapor molecules 103 that had been sorbed onto coating 101b on wire 101a will be rapidly desorbed from heated wire 101a and will be resorbed onto room-temperature wire 101b. In some cases, vapor molecules 103 may include one or more types of molecules 104 that are sufficiently less volatile at the temperatures/coatings used that they do not participate in the desorb/transfer process and, as illustrated in FIG. 1B, such molecules may remain on the heated wire 101a.

This process continues so that, at time t=2Δt shown in FIG. 1C, wire 101b is rapidly heated (with wires 101a and 101d also remaining heated) while wire 101c is rapidly cooled, which causes molecules 103 to be desorbed from coating 102b on wire 101b and be sorbed by coating 102c on wire 101c. Finally, and at time t=3Δt shown in FIG. 1D, wire 101c is rapidly heated (with wires 101a and 101b also remaining heated) while wire 101d is rapidly cooled to cause the molecules 103 to be desorbed from coating 102c on wire 102a and be sorbed by coating 102d on wire 101d. When the analyte vapor reaches a wire sufficiently close to an unheated sensor 106, that wire can be abruptly heated to cause the analyte vapor to desorb from the wire and thereby arrive at the sensor for detection.

Thus, in accordance with the present invention, by applying and removing heat from the wires in such a phased heating schedule, a controlled sorption/desorption process can be obtained which moves molecules from wire 101a to wire 101d in a desired manner without the need for a clean carrier gas or pumping of the vapor by a pressure head. In other words, this thermal ratcheting scheme produces the desired molecular drive with a greatly reduced diffusion overhead.

The thermal ratcheting method of this invention as just described can be utilized as an apparatus serving the practical purpose of collecting, concentrating, and transporting analyte molecules from the ambient to a sensor. In an exemplary embodiment, such an apparatus can be in the form of a concentric ring concentrator as illustrated in shown in FIG. 2, though, as described below other two- and three-dimensional configurations may be possible within the scope of the present invention.

Figure 2:
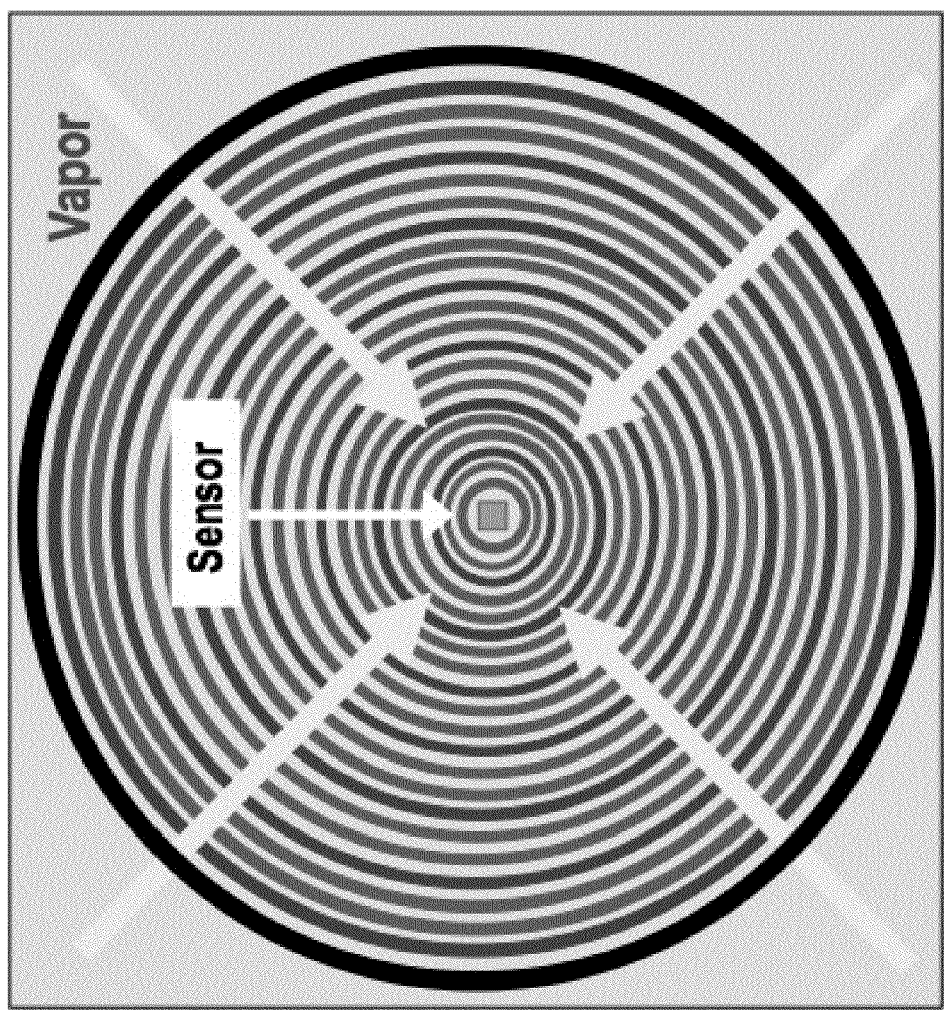
FIG. 2 is a block diagram illustrating aspects of an exemplary embodiment of a molecular concentrator based on thermal ratcheting in accordance with the present invention.

As illustrated in FIG. 2, such an apparatus can consist of a micro-fabricated two-dimensional circular configuration of concentric closely-spaced wire heating elements, with a sensor element located at the center of the circular arrangement of wires. In some embodiments, the wires can be situated directly on a substrate, while in others they can be suspended above the substrate to improve the thermal isolation of each wire from the others. The surfaces of the wires may be bare metal or may be treated to alter the surface roughness and/or chemical composition for the purpose of enhancing the quantity and/or selectivity of the vapor sorption. The surfaces of the wires may also be coated with a thin film designed to sorb vapors into its matrix for the purpose of further enhancing the quantity and/or selectivity. The thickness of such coatings may range from a molecular monolayer (~0.5 nm) to a thin film (~0.1 mm). The apparatus' overall dimension may range from the $mm^2$ to $cm^2$ scale, with the width and spacing between the electronic wire heating features ranging from under a micron to a millimeter or more.

Each of the individual wires in the wire pattern is connected to a current source configured to selectively apply current to individual wires to cause the wire to become heated through resistive heating when the current through the wire is turned on, and then to return to room temperature when the current through the wire is turned off. Thus, in accordance with the present invention, by the application of appropriately phased heat pulses such as the phased heating depicted in FIGS. 1A-1D, molecules in a vapor incident on the wire structure are driven from the periphery of the structure to the sensor located at the center. The converging nature of the design leads to a geometrical concentration of any molecules in the ambient that are sorbed at the periphery and are capable of following the sorption/desorption cycles at the selected temperatures and frequencies for the sorption-desorption characteristics of a particular coating.

In addition, by appropriately configuring one or more of the arrangement of the wires, the coating thereon on the wires, and the temperatures or times applied, the composition of the molecules moved from wire to wire can be selectively tuned, e.g., to enhance the concentration of molecules of interest and/or to suppress the concentration of interferent molecules reaching the sensor.

In embodiments where a surface treatment or a coating is applied to the heater wire surface, the treatment/coating can be designed to have an affinity for a targeted vapor of interest and/or to provide enhancement of quantity and selectivity of sorbed vapors by way of reversible chemical interactions.

Such surface treatments or coating depositions position a density of molecular sites onto the wire surface or within the thin film matrix of the coating that have an affinity to or interact with vapors of interest and serve as sites for vapor adsorption on the treated surface or for vapor absorption within the matrix of the film. Both the density and binding strength of such vapor sorption sites exceed those of the bare metal heater wire surface.

A degree of selectivity for targeted vapors may also be included in the design of a surface treatment or a coating for vapor sorption. The types of reversible chemical interactions include acid-base, hydrogen bonding, charge-transfer, dipole-dipole, and van der Waals. Physical and chemical processes for surface treatments include energy beams (laser, electron, ion beams), plasmas (various gas phase chemicals), and chemical depositions (organometallic chemical vapor depositions, atomic layer depositions, self-assembled monolayers).

Thin film coatings include a variety of organic polymers (many classes of thermoplastics, elastomers, and thermosets), inorganic polymers (several classes), non-volatile small molecules and salts, and these coatings may be deposited by self-assembly from vapor or solution phases, solution aerosol deposition, mechanical transfer, or vapor deposition polymerizations. In thickness these thin films may be monomolecular layers (0.5 nm thickness) onto which analyte vapors may selectively adsorb or thicker film depositions (up to 0.1 mm) into which analyte vapors may absorb.

The key requirements are that the surface treatment or coating film be compatible with the concentrating apparatus of this invention, have a thermal stability over the temperature range of operation, and have a reversible interaction (sorption and desorption) with vapors of interest over the temperature range of operation.

While examples of the above-mentioned general surface treatments and thin film coatings have been described, it should be obvious to those skilled in the art that any surface treatment or coating that complies with the above key requirements is practicable in this invention.

For example, gold surfaces can be treated with a pulsed argon ion beam which will cause surface roughening and some oxide formation. See B. H. Kear, J. W. Mayer, J. M. Poate, and P. R. Strutt, "Surface Treatments Using the Laser, Electron and Ion Beam Processing Methods," *Metall. Treatises* (J. K. Tien and J. F. Elliott, eds.), 1981, pp. 321-343. This increase in surface area and surface energy has a significant effect on adsorption of vapors.

In other cases, a nitrogen or oxygen plasma surface treatment of aluminum or other metals causes pitting of the surface and significant incorporation of nitrogen or oxygen. See M. C. Kim, S. H. Yang, J.-H. Boo, and J. G. Han, "Surface treatment of metals using an atmospheric pressure plasma jet and their surface characteristics," *Surface and Coatings Technology*, 2003, 174, 839. This treatment for similar reasons enhances adsorption of vapors.

When using an OMCVD deposition, volatile organometallic compounds react with and deposit material onto a surface, or, more selectively, atomic layer deposition (ALD) can be used to deposit alternating layers of chemically reacting constituents onto a surface. These methods can accommodate large variations in chemical composition of the surface deposition but are not very localized to deposition onto the heater wire features of the device.

Chemical self-assembly is a more controlled mode of deposition where a chemical functionality of a deposited molecule bonds to the metal surface. The most frequently used example is the thiol functional group on an organic molecule that chemically bonds to a gold atom on the metal surface. This feature localizes the deposition to the heater wire and can be done from the vapor phase as well as solution. It also offers the option of putting an additional functional group on the organic molecule for a specific interaction with a target vapor. A good example is the carboxylic acid functionalized alkanethiol where the thiol group bonds to an atom in the gold surface. The —COOH groups form ammonium-carboxylate complexes with amine vapors at room temperature, and this complex dissociates at temperatures between 50 and 100° C. See A. W. Snow, G. G. Jernigan, and M. G. Ancona, "Packing density of $HS(CH_2)_nCOOH$ self-assembled monolayers," *Analyst* 2011, 135, 4935; see also M. G. Ancona, A. W. Snow, F. K. Perkins, B. Pate, and D. Park, "Analyte kinetics in a nanocluster-based chemiresistor: A case study," *Sensors and Actuators* B 177, 936-946 (2013) ("Ancona 2013"), both of which are incorporated by reference into the present disclosure in their entirety.

The use of polymer films thousands of monolayers in thickness (approaching 0.1 mm) accommodates a much larger quantity of vapor by way of an absorption into the interior of the film instead of an adsorption on the film's outer surface. If a vapor-complexing functionality is incorporated into the structure of this polymer film, the absorption quantity of vapor is further enhanced, and a complex formation and thermal release mechanism can be built into the thermal ratcheting device. For work reported in this specification, a linear epoxy polymer based on 1,4-cyclohexanedimethanol diglycidyl ether, 4-(4-aminophenyl)butyric acid and aniline in a 2:1:1 molar ratio and triethylamine (TEA) as the interacting vapor is used. This system utilizes the formation and thermal dissociation of the ammonium-carboxylate complex as part of an experimental demonstration of a reduction to practice for the thermal ratcheting device. However, it should be obvious to those skilled in the art that many other thin film vapor sorbent coatings and complementary vapors can function in this manner when employed in the thermal ratcheting device. Among such coatings would be those utilized in the fields of gas chromatography and surface acoustic wave sensor technology. See, e.g., A. Voelkel, "Inverse Gas-Chromatography—Characterization of Polymers, Fibers, Modified Silicas, and Surfactants," *Crit. Rev. Anal. Chem.* 1991, 22, 411-439; and G. M. Gross, V. R. Reid, and R. E. Synovec, "Recent Advances in Instrumentation for Gas Chromatography," *Curr. Anal. Chem.* 2005, 1, 135-147.

The structures illustrated in FIGS. 1A-1D and FIG. 2 capture the basic principles of the thermal ratchet method and apparatus for analyte collection and delivery. However, an actual implementation must also contend with certain limitations imposed by kinetic theory, thermodynamics, and chemistry. One such limit is the conflict between a desire to get the wires close together for efficient transfer and the need to keep them thermally isolated so that their temperatures can be manipulated independently. One approach is to make substrate 105 be a material like $SiO_2$ that has a very low thermal conductivity. A better isolation approach is to suspend the wires as air bridges, e.g., supported by widely separated posts defined on the substrate, in which case the dominant inter-wire coupling is from the weak thermal conduction through the air.

Figure 3:
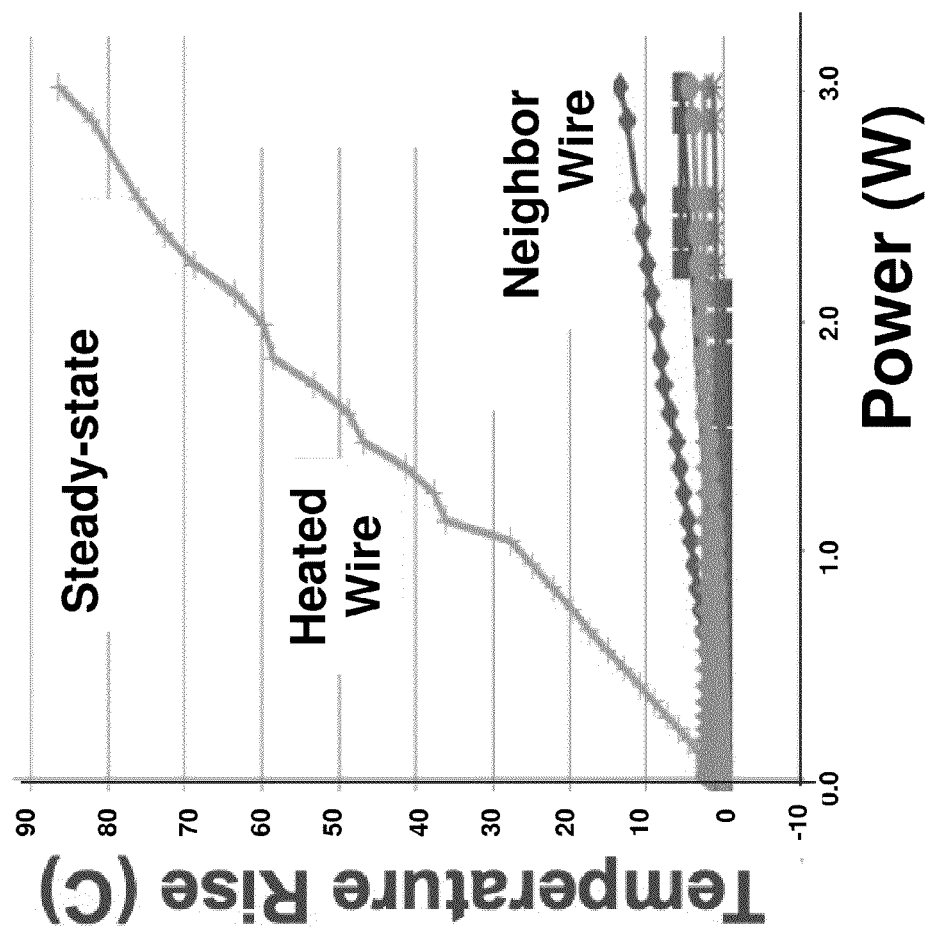
FIG. 3 is a plot illustrating aspects of suspended wire heating utilized in a molecular concentrator based on thermal ratcheting in accordance with the present invention.
Figure 4:
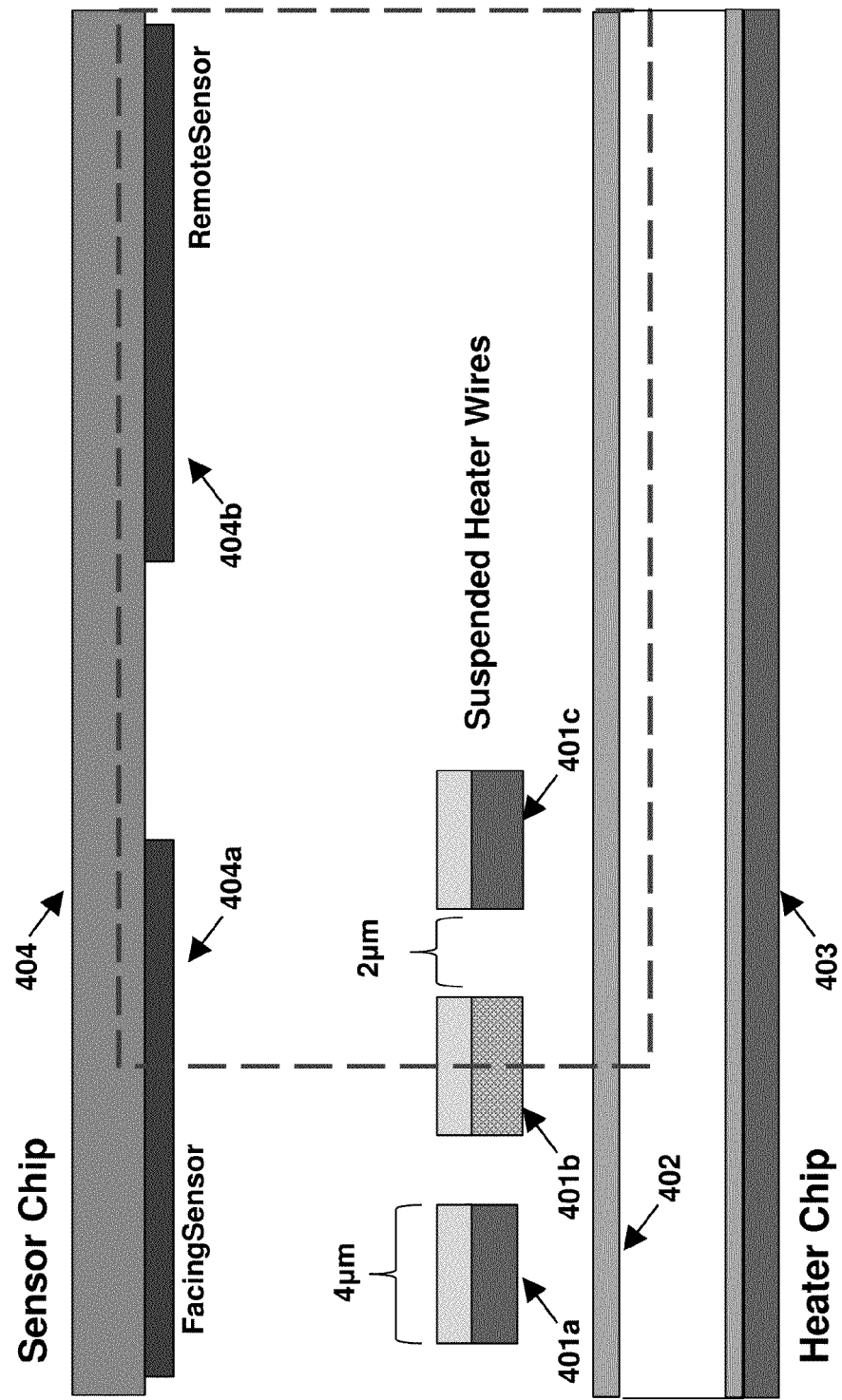
FIG. 4 is a block diagram illustrating aspects of an exemplary embodiment of a molecular concentrator based on thermal ratcheting in accordance with the present invention.

A plot illustrating an experimental demonstration of the thermal isolation possible with this strategy is presented in FIG. 3 where the steady-state temperatures of a heated wire and of its neighbors (with the nearest parallel neighbor being about 1 μm distant) is plotted as a function of the applied power.

A critical issue regarding the thermal-ratchet idea relates not to its performance but to proving its operation. This is a challenging task given the trace amounts of analyte and the micron-scale geometries, and therefore to demonstrate the thermal-ratchet method as well as to understand some of its design issues a variety of numerical simulations and experiments are performed.

That the system of heated wires is on a scale that is large compared to the mean free path in air (~60 nm) with a Knudson number less than 0.1 means the analyte desorption and flow can be modeled using the compressible Navier-Stokes equations with the analyte transport treated using a convection-diffusion equation and the boundary conditions describing the heater wire temperatures and the desorption. In an exemplary flow regime, viscous effects tend to dominate with the Reynolds' number Re of roughly 0.1 and the importance of thermal effects is measured by an estimated Prandtl number Pr of about 0.7.

The equations governing the motion of the molecules across the wires are then the conservation of air mass $$\frac{dc}{dt} + c\nabla \cdot u = 0,$$

the conservation of momentum in the air $$mc\frac{du}{dt} + \nabla \cdot \left(pI - \mu\nabla u + \frac{2}{3}\mu I\nabla \cdot u\right) = 0,$$

the convection equation for the analyte molecules in the air $$\frac{da}{dt} - \nabla \cdot (D_a \nabla_a) + a\nabla \cdot u = 0,$$

and the heat conduction equation $$mcC_v \frac{dT}{dt} - \kappa \nabla^2 T = 0,$$

where t is time; p is the air pressure, μ is the air viscosity, c is the local air density, and u is the local air velocity; m is the average atomic mass of the air molecules; a is the density of analyte molecules and $D_a$ is the diffusion constant; I is the identity matrix; T is the local temperature, $C_v$ is the specific heat of the air, and κ is its thermal conductivity.

Figure 5:
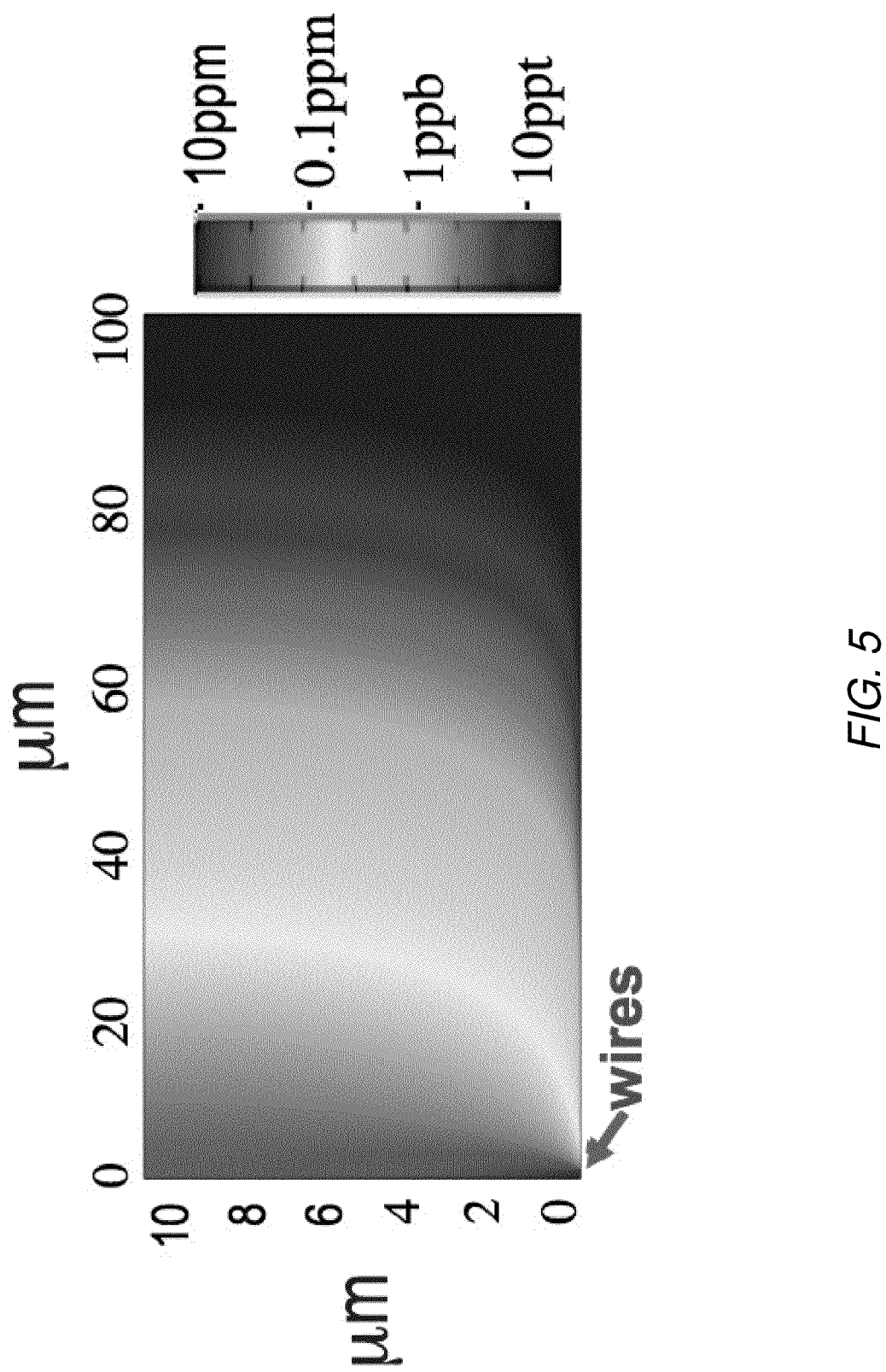
FIG. 5 is a plot showing a simulated concentration profile following the heating of a single wire having an initial sub-monolayer coating of adsorbed analyte in accordance with the present invention.

The absorption/desorption kinetics of the molecules as they interact with the heated/cooled wires in accordance with the present invention can be expressed as $$\frac{\partial s}{\partial t} = k_s(r_s a - s) - n \cdot J_a,$$

with the Maxwell-Smoluchowski slip condition being expressed as $$u = \frac{2-\sigma_v}{\sigma_v} \frac{u\partial u/\partial y}{c\sqrt{2RT/\pi}} + \frac{3}{4} \frac{C_v \mu(\gamma-1)}{cRT} \frac{\partial T}{\partial x},$$

where c, κ, T, and $C_v$ are as above; s is the adsorbed analyte density, $\sigma_v$ is the momentum accommodation factor related to surface roughness of the wires; $k_s$ and $r_s$ are reaction rate constants; $J_a$ is the flux of adsorbing analyte; n is the surface normal vector; u is the slip velocity at the surface; γ is the ratio of specific heats; x and y are the coordinate directions implicit in FIG. 5 with x horizontal and y vertical; and R is the ideal gas constant.

To examine the basic behavior of molecules in a thermal ratcheting molecular concentrator in accordance with the present invention, the inventors used the above model to simulate numerically a molecular concentrator having the exemplary structure illustrated in FIG. 4.

As shown in FIG. 4 such an exemplary structure consists of three long adsorbent material-coated heater wires 401*a*/401*b*/401*c* (shown in cross-section in FIG. 4). To prevent the heating of one wire by neighboring wires, the wires are modeled as being suspended over a substrate 402 and separated from one another by a distance of 2 μm as shown in the FIGURE. As described above with respect to FIG. 1A-1D, in accordance with the present invention, wires 401*a/b/c* are resistively heated by means of an electric current passing therethrough, e.g., from heater chip 403 shown in FIG. 4, and then are brought back to room temperature to cause vapor molecules to be sorbed/desorbed and thus moved along from one wire to another. Opposite and parallel to heater chip 403 is a sensor chip 404 containing sensors that in the experiments serve to monitor the thermal-ratchet operation. These sensors include a facing sensor 404*a*, which is situated directly above and facing the suspended wires, and a remote sensor 404*b*, which is situated at some distance away from the suspended wires.

A snapshot from a simulation of this structure is shown in the contour plot in FIG. 5, which displays the concentration of an analyte of interest in a plume of analyte vapor emitted following abrupt heating of an analyte-loaded wire. As is clear from the plot, the greatest concentration of analyte reaches the sensors (which reside on the top surface of the plot, and with the facing sensor at the left edge) where they approach most closely to the heated wire. From numerous calculations of this type the thermal-ratchet action can be captured in the computer and its characteristics studied including the expected response signals that would be measured by the sensors.

The summary plots shown in FIGS. 6A-6D show the efficiency of transfer of molecules at each step from a suddenly heated wire onto a cold neighboring wire under specified conditions and assuming no sidewall adsorption.

The effect of the time allotted for the transfer is presented in FIG. 6A. The transfer efficiency is lower if a shorter time is available for the molecules to move and is greater when a longer time is available, and if sufficient time is available, the transfer efficiency can be quite high (e.g., >90%).

The thermal-ratchet can be used to obtain selectivity by distinguishing molecules according to their volatility and coating sorptive affinity. Such selectivity can be obtained either by controlling the temperature to which the wires are heated, as shown in FIG. 6B or by controlling the switch time, as shown in FIG. 6C. In each case, the transfer efficiency is seen to depend on desorption energy. By proper choice of the temperature and switch time, analyte separation can be effected based on differing desorption energies. In this process, the constituent vapor with the lower desorption energy is driven forward by the thermal ratchet, while the constituent with the higher desorption energy remains adsorbed to the heater wires.

A final summary plot in FIG. 6D shows the ability to concentrate the analyte vapor that the concentric ring concentrator shown in FIG. 2 would be expected to exhibit. The two curves shown in FIG. 6D correspond to two different modes of sequencing the heat pulses applied to the heater wires. The "pulsed" mode is identical to that depicted in FIGS. 1A-1D in which the wires are heated and cooled in sequence. In contrast, in the "tidal wave" mode, once wires are heated they are left heated so that a step in wire heating propagates inward through the concentrator, pushing analyte on to the unheated wires before it and toward the sensor at the center. These plots demonstrate that, irrespective of the number of wires used, the "tidal wave" mode of heating the wires is more efficient than the "pulsed" mode, though in both cases substantial levels of molecular focusing are seen to be possible.

To further demonstrate the invention, experimental results focused on the basic thermal ratchet mechanism by which the analyte transfer are depicted in FIGS. 1A-1D. For this purpose, a combined heater-sensor configuration such as that illustrated in FIG. 4 was used, with a second sensor chip placed parallel to the chip with the heater wires at a variable distance. This chip enabled the molecular action to be monitored using two sensors, one a "facing" sensor that is situated immediately across from the heated wires and the other a "remote" sensor positioned a few millimeters away. For these experiments, triethylamine (TEA) vapor is used as a test analyte, the adsorbent material on the heater wires is a carboxylic acid (COOH)-functionalized amine-epoxy polymer coating, and the sensors are MIME chemiresistors based on a thin film of gold nanoclusters having a passivating surface ligand composed of mercaptohexanoic acid. For a discussion of the COOH-amine chemistry in a sensor context, see Ancona 2013 supra. Among other things, this paper shows that the MIME sensor made with gold nanoclusters coated with mercaptohexanoic acid is extraordinarily selective for amines like TEA, and highly sensitive with a minimum detectable level below 1 part per billion (1 ppb).

Figure 7:
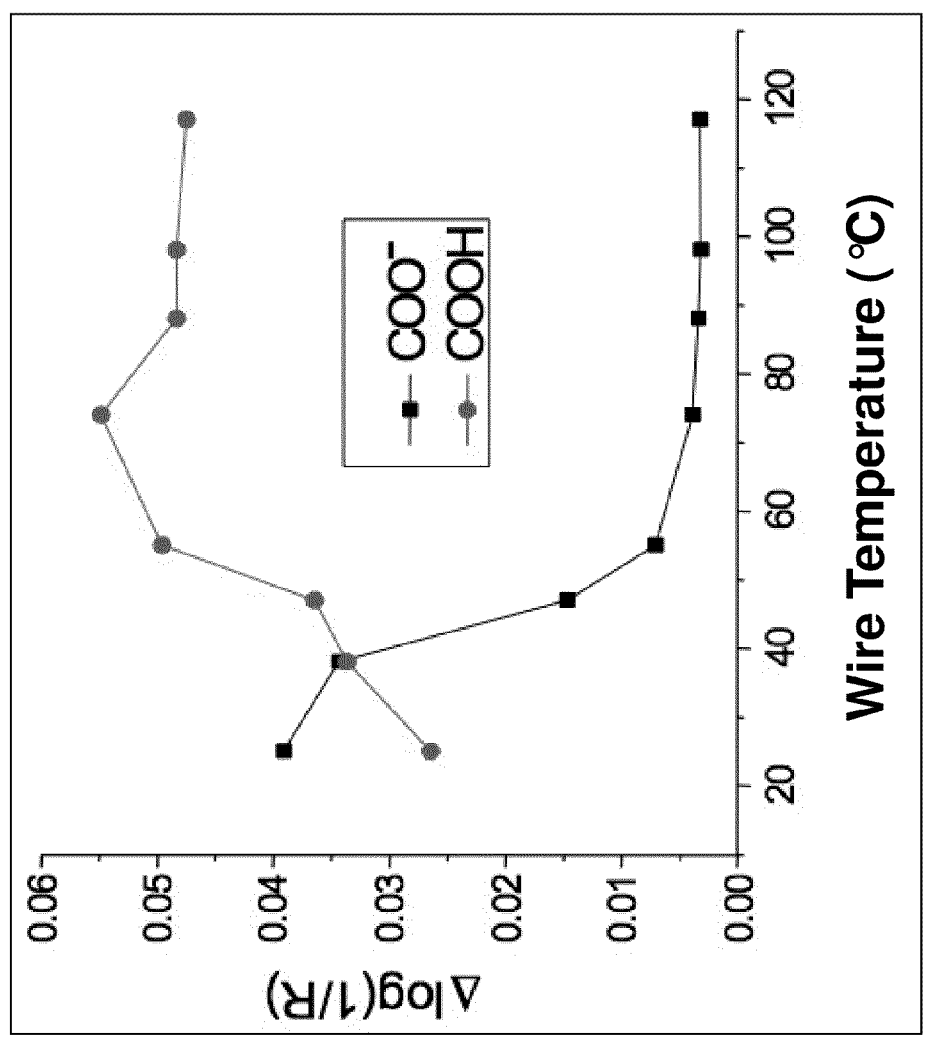
FIG. 7 is a plot showing the results derived from Fourier transform infrared spectroscopy (FTIR) analysis of an exemplary COOH-functionalized epoxy film exposed to a triethylamine (TEA) analyte in accordance with one or more aspects of the present invention.

FIG. 7 depicts the TEA absorption characteristics of the COOH-functionalized epoxy polymer film used as the coating/absorbent covering the heater wires in the specific test implementation of the present invention under discussion. The traces shown in the FIGURE correspond to the amounts of carboxylic acid (COOH) and carboxylate (COO—) groups in the film following exposure to TEA as measured by Fourier transform infrared (FTIR) spectroscopy (and specifically the reflectivity R) as a function of the wire temperature. FIG. 7 shows that, as the film is heated above a temperature of about 40° C., there is a disappearance of COO— groups and an appearance of COOH groups in the film. This is a consequence of departure of the TEA vapor from the absorbed ammonium-carboxylate complex and leaving behind the re-protonated polymer —COOH functional group. This demonstrates that the COOH-functionalized epoxy coating has the desired property of being both a good sorber of the analyte TEA at room temperature and a good desorber of the TEA when temperature is raised by an amount readily accessible through resistive heating.

To examine what might be observed in the experiments performed on the heater-sensor test structure under discussion, two additional simulations are performed by solving the compressible Navier-Stokes equations given earlier. Both simulations are based on an initial state in which a 0.1 monolayer of TEA was adsorbed onto a center heater wire.

Figure 8B:
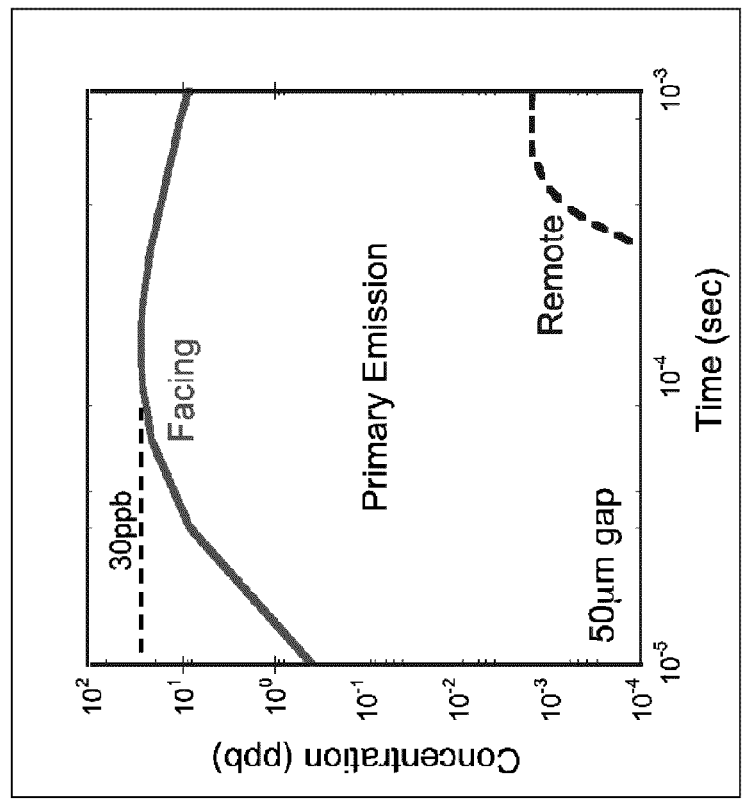
FIGS. 8A and 8B are plots showing a simulated response of the facing and remote sensors due to a pulse of analyte emitted from a heater wire covered with a layer of TEA and then abruptly heated (primary emission).
Figure 8A:
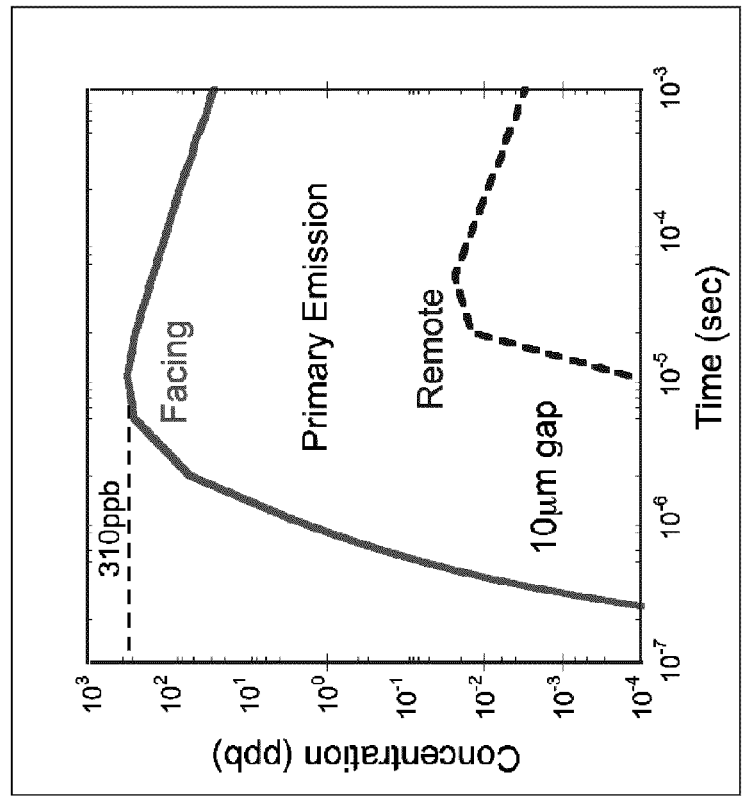

In the first simulation, the center wire was heated to form a "primary emission" consisting of the burst of the desorbed analyte from the heated wire. The simulated sensor responses to this primary emission for the "facing" and "remote" sensors on the sensor chip were collected as a function of time as shown in FIGS. 8A and 8B, where FIG. 8A plots the measured analyte concentration for a sensor chip situated 10 μm away from the heater chip and FIG. 8B plots the concentration for a sensor chip situated 50 μm away. All of the plotted concentrations are well within the known detection range of the MIME sensors for TEA (<1 ppb as noted earlier). Evident in the plots is the expected result that the concentration measured at the "remote" sensor peaks both more slowly and to a smaller magnitude than that seen on the facing sensor, and this is true irrespective of the distance between the sensor chip and the heater chip. As also would be expected, the narrower (10 μm versus 50 μm) gap between the sensor and heater chips provides a higher measured analyte concentration because the ambient volume into which the initial analyte concentration from the wire is diluted is smaller.

Figure 6A:
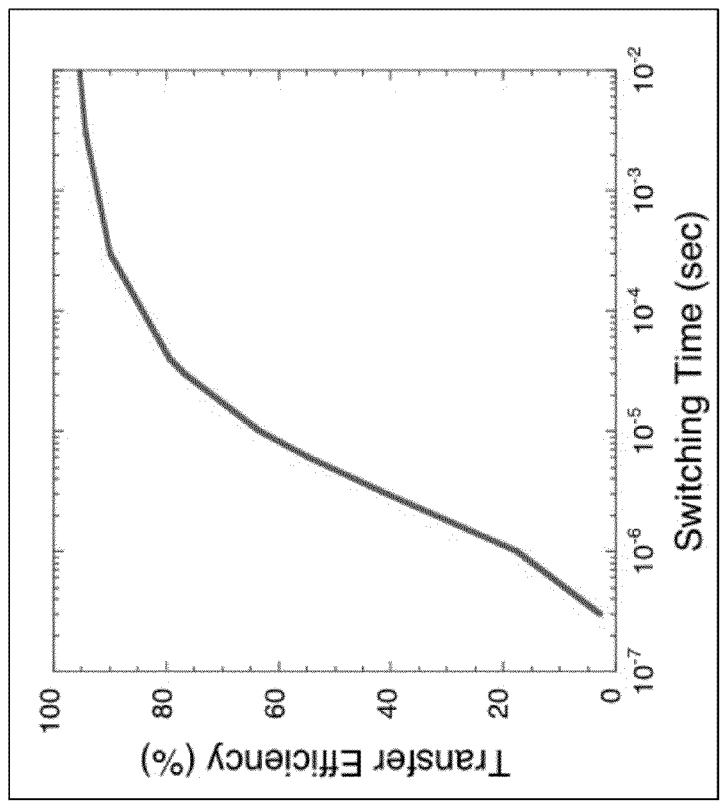
FIGS. 6A-6D are plots showing simulated aspects of analyte transfer and concentration in accordance with the present invention.
Figure 6B:
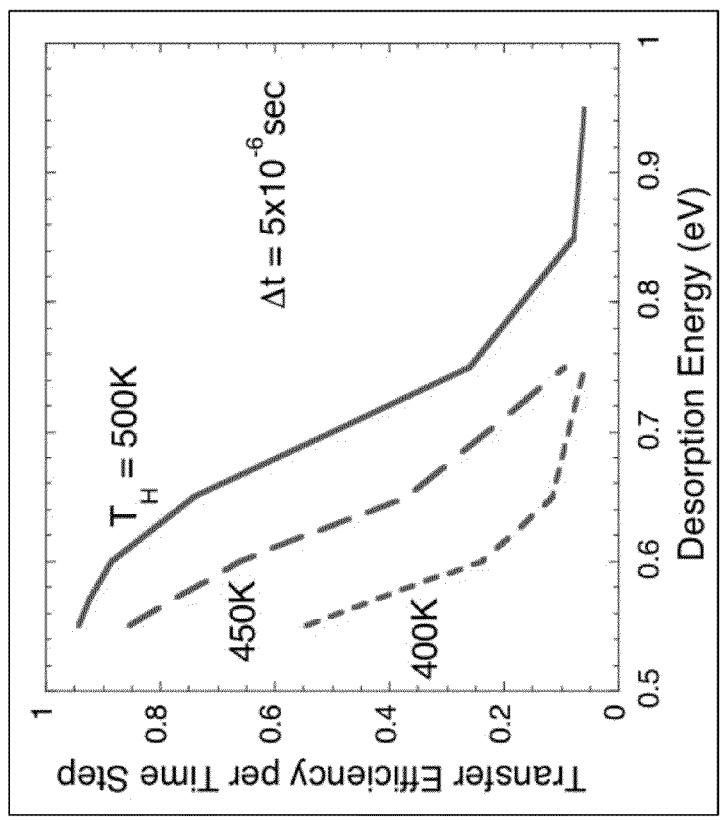
Figure 6D:
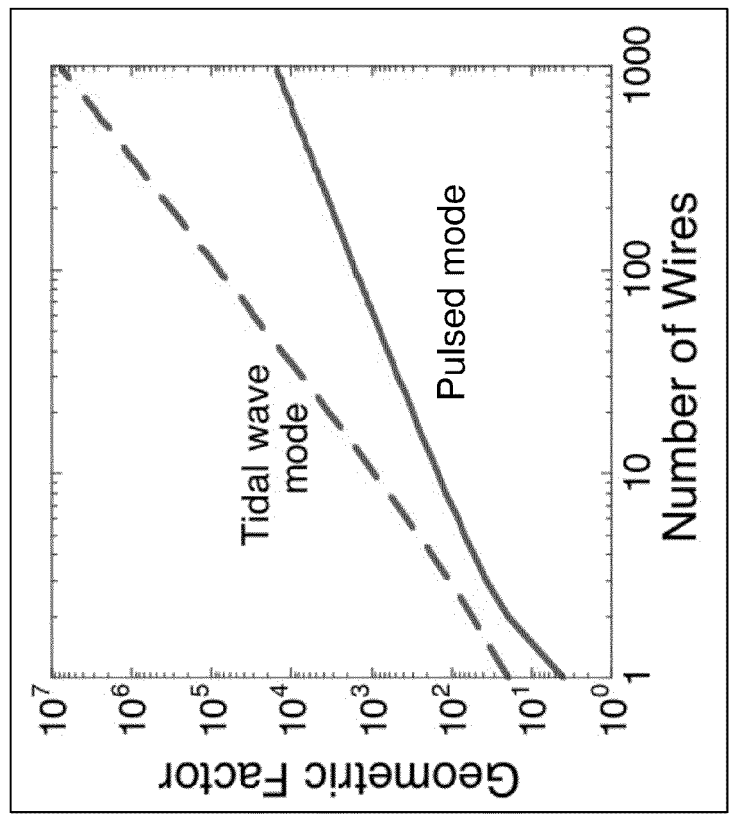
Figure 6C:
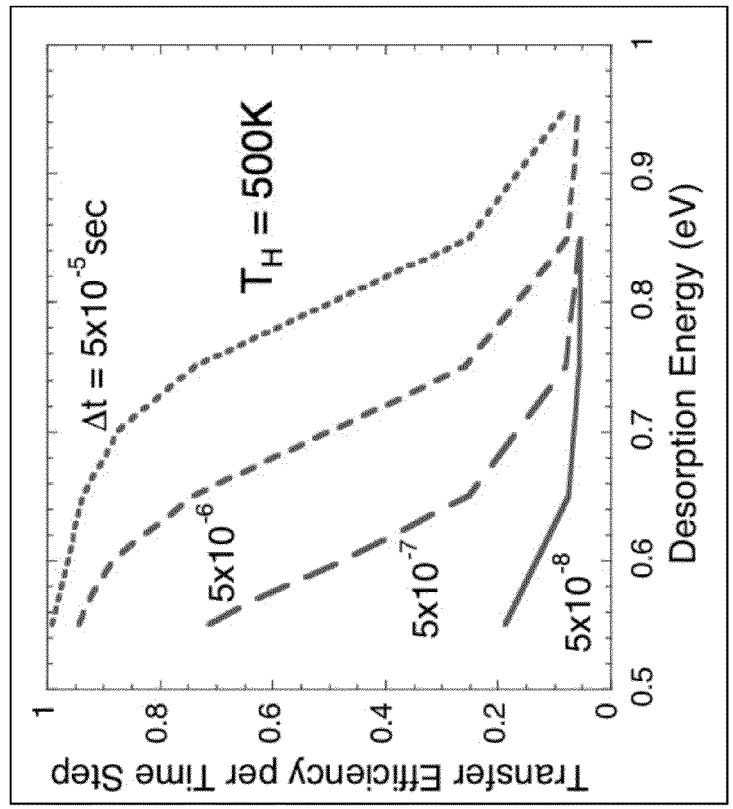

The second set of simulations models the crucial proof-of-principle experiment of the present invention that demonstrates the thermal ratchet mechanism by examining the elementary step of molecules being transferred from one wire to another. The simulation again begins with analyte adsorbed on the center wire. The center wire is then rapidly heated, and, as described above, the analyte is desorbed form the heated wire to form a primary emission of analyte. In addition, as studied in the simulation that produced the "transfer efficiency" plot shown in FIG. 6A and as described above with respect to FIGS. 1A-1D, in accordance with the present invention, some of the desorbed analyte will be re-adsorbed on neighboring cold wires, i.e., will effect the desired transfer of molecules from one wire to another. To demonstrate that this transfer occurs, one of the neighboring wires is rapidly heated and any transferred analyte is desorbed from that wire forming a "secondary emission" is measured by the sensors.

Figure 9B:
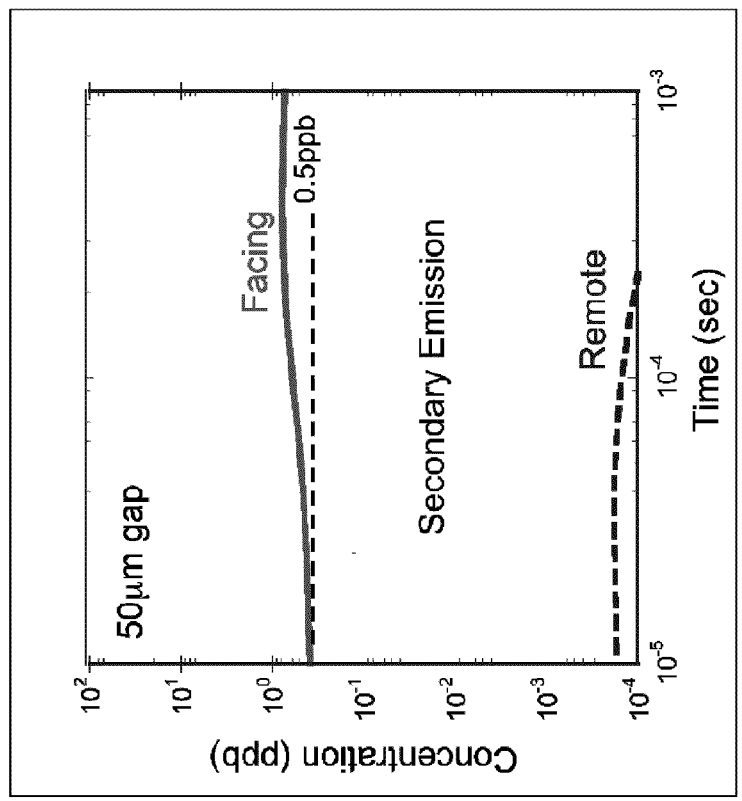
FIGS. 9A and 9B are plots showing a simulated response of the facing and remote sensors due to a pulse of analyte emitted by an abruptly heated second heater wire to which TEA analyte had previously been transferred from a first heater wire (secondary emission).
Figure 9A:
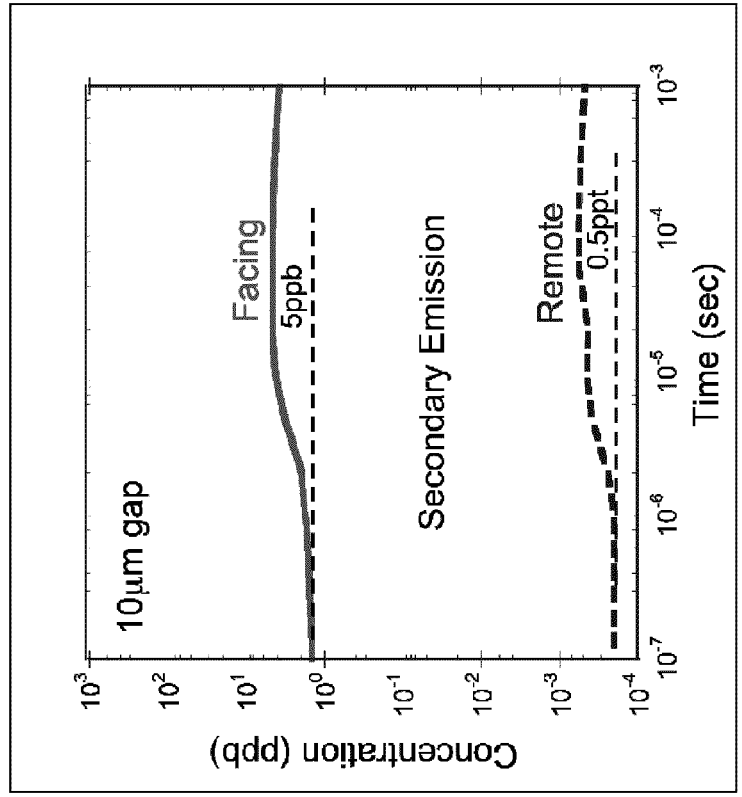

The simulated sensor responses associated with such a secondary emission are shown in FIGS. 9A and 9B for heater-sensor gaps of 10 μm and 50 μm, respectively. In both cases only the facing sensor detects an appreciable level of analyte, with the measured response consisting of not only the secondary emission plume associated with the heating of the second wire but also a background associated with the primary emission previously desorbed from the first wire. The plots in FIGS. 9A and 9B show the levels of detected analyte associated with the secondary emission are quite small—0.5 ppb for a facing sensor 10 μm from the heater chip and 0.5 ppb for a facing sensor 50 μm away—but are still large enough to be detected by a high-performance sensor such as the MIME sensor described above.

FIGS. 10A and 10B show measured sensor responses for the facing sensor in an experiment looking at the primary emission of TEA from a suddenly heated wire as studied previously in simulation in FIGS. 8A and 8B. In this experiment, a single wire was loaded with TEA simply by heating all of the wires except the center one during exposure to the vapor analyte. A heat pulse applied to this wire produced the primary emission that was then monitored using the sensor. This measurement was made more complicated by the fact that the heater wire pulse raises the temperature of the nearby sensor slightly (by about 0.15 C, and primarily due to heat conduction through the air) and that in itself produces a sensor response (see FIG. 10A). However, the thermal response and the response to the TEA are opposite in sign, with the former relatively abrupt and fixed in magnitude, and so the two signals can readily be distinguished. The TEA response alone (with the thermal response subtracted off) is plotted in FIG. 10B, and the measured magnitudes and temporal behavior are quite similar to the simulated behavior plotted in FIGS. 8A and 8B.

In both FIGS. 10A and 10B the multiple traces are associated with sequential heat pulses. The TEA signal is observed to drop with each successive pulse as the TEA on the wire becomes increasingly depleted. Thus, the MIME sensors in the heater-sensor test structure are experimentally demonstrated to detect the TEA analyte emitted from a single heated wire.

Figure 11:
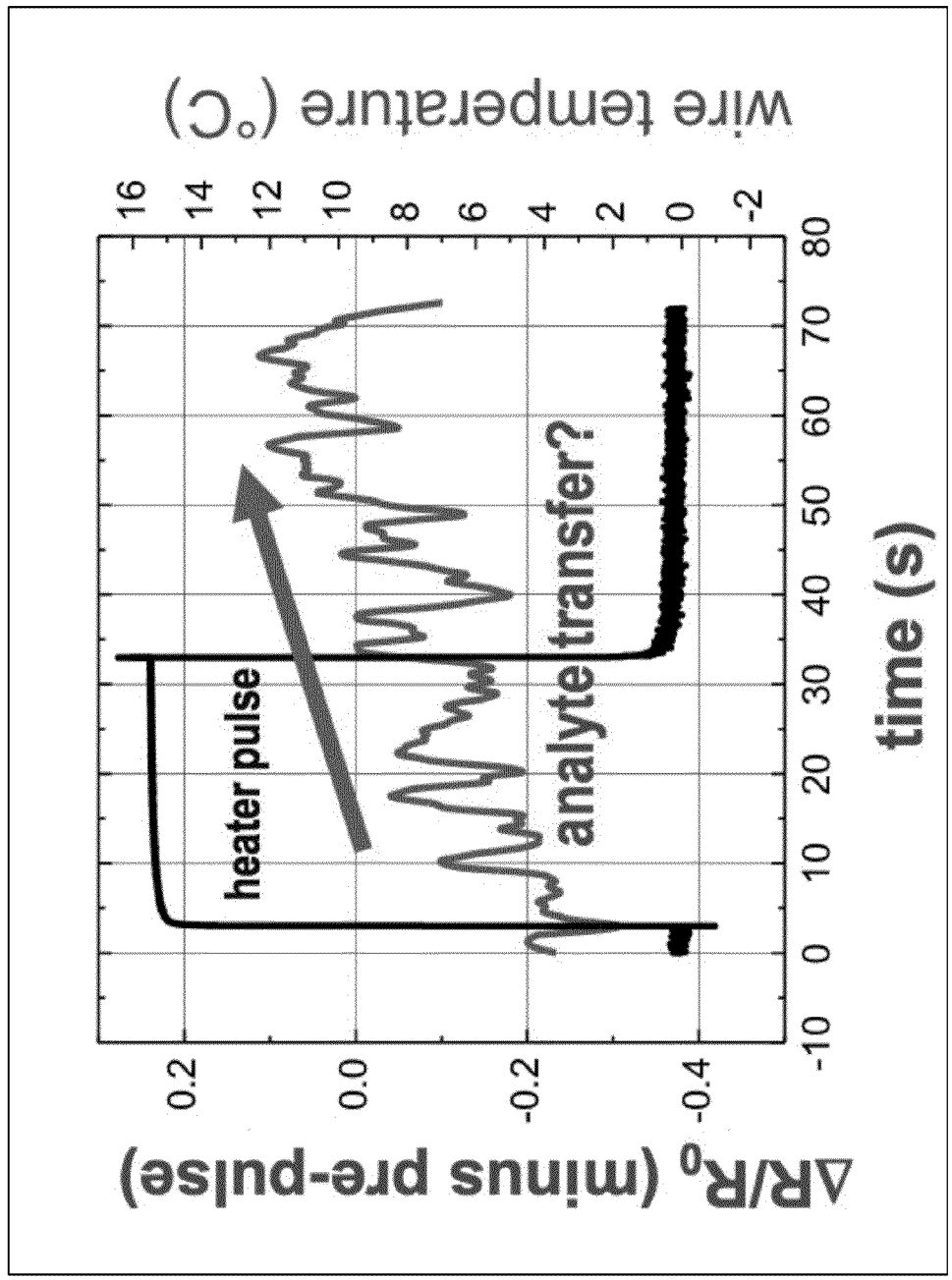
FIG. 11 is a plot showing measured sensor characteristics for the facing sensor in response to (secondary) emission of TEA in accordance with the present invention.

The plot in FIG. 11 shows results from the proof-of-principle experiment examined previously in simulation in FIG. 9. The objective of this experiment is detection of the "secondary emission" from a suddenly heated wire of the TEA that had previously been transferred to it from a neighboring wire using the thermal-ratchet mechanism. FIG. 11 displays the heater wire pulse (the black line and the right-hand axis giving the change in wire temperature) lasting from time=3 sec to time=32 sec, and the facing sensor response to the TEA with the thermal background subtracted off as in FIG. 10B. A response appears both during and following the heater pulse, and in accord with the simulations in FIG. 9 it is quite small (though still above the detection limit of the sensor). That a secondary emission response seems to be observed is experimental evidence in support of the proof-of-principle notion that analyte transfer between wires is observed and that the underlying thermal-ratchet mechanism is indeed capable of driving molecules.

In summary, the present invention teaches a unique method based on a thermal ratcheting mechanism for moving molecules on a substrate with a much reduced diffusion loss and teaches an apparatus for exploiting this mechanism to concentrate, separate, and transport chemical vapor analytes to a sensor component. In an exemplary embodiment, the apparatus is in the form of a concentric ring concentrator that directs ensembles of molecules into a very small region for purposes of transduction and detection, but one skilled in the art will readily recognize that other configurations may be possible.

FIGS. 12-16 illustrate aspects of some of such additional molecular concentrator embodiments that offer alternative implementations of the ratchet mechanism and could be advantageous in providing more efficient delivery, higher levels of concentration, or possibly other benefits. These embodiments are illustrations of several new design approaches that are described further below.

In these additional embodiments, the molecular concentrator can comprise one or more two-dimensional or three-dimensional arrangements of heating elements. In the case of embodiments having more than one arrangement of heating elements, such multiple arrangements can be comprise two or more two-dimensional arrangements or two or more three-dimensional arrangements, where the two or more arrangements are configured to be either co-planar or non-coplanar with respect to one another, or can be in the form of a combination of two- and three-dimensional arrangements.

Some of these embodiments are described below. However, one skilled in the art will readily recognize that other two- and three-dimensional arrangements and configurations are possible, and all such arrangements and configurations of heating elements are deemed to be within the scope of the present disclosure.

Figure 12:
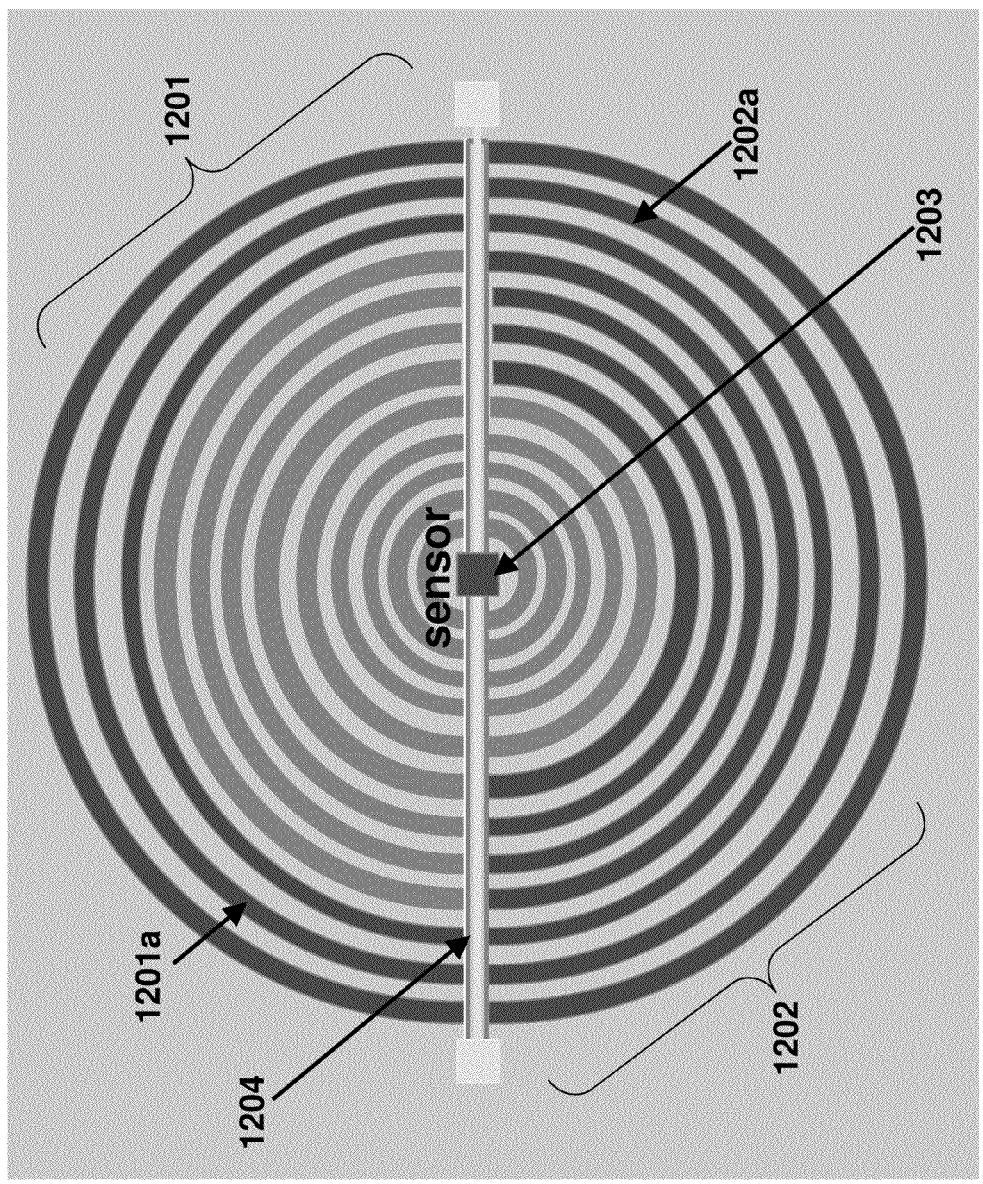
FIG. 12 is a block diagram illustrating aspects of another exemplary embodiment of a molecular concentrator based on thermal ratcheting in accordance with the present invention.
Figure 13:
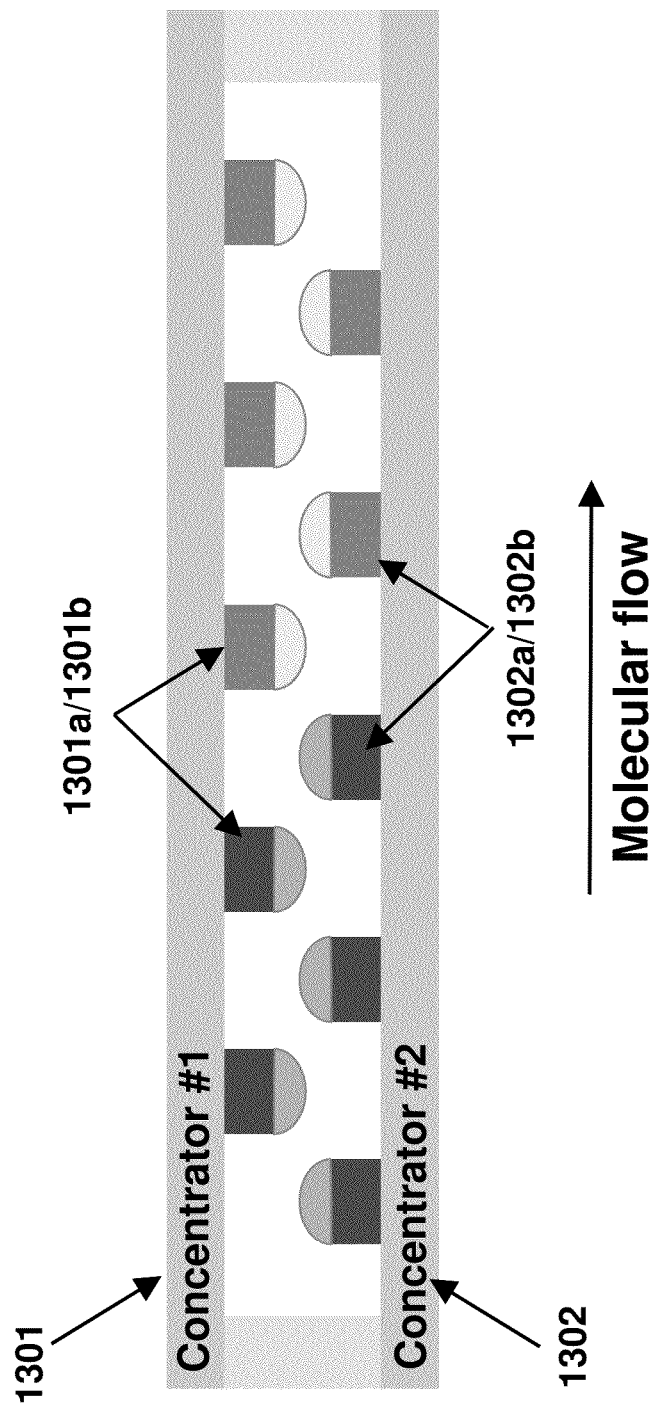
FIG. 13 is a block diagram illustrating aspects of another exemplary embodiment of a molecular concentrator based on thermal ratcheting in accordance with the present invention.

2-D Designs:

FIGS. 12 and 13 illustrate aspects of some of these additional configurations that retain the two-dimensional geometry of the concentric ring design and thus continue to be amenable to conventional planar fabrication techniques such as optical/e-beam lithography, wafer-bonding, etc.

The embodiment illustrated in FIG. 12 is similar to the embodiment illustrated in FIG. 2, but instead of being arranged in a series of concentric rings, the heater/absorber wires of the embodiment illustrated in FIG. 12 are configured in a semicircular arrangement. Thus, as shown in FIG. 12, a molecular concentrator in accordance with this embodiment of the present invention can include one or more collectors 1201/1202, each comprising a corresponding plurality of semicircular heater/absorber wires 1201*a*/1202*a* arranged concentrically around a shared sensor element 1203 that is contacted by the wires 1204. Each of the collectors 1201/1202 is independent from the other one and can have a different heating sequence or otherwise be optimized for a different purpose. The heater/absorber wires are heated and cooled as described above to direct analyte molecules to the sensor.

One use of an arrangement as in FIG. 12 would be simply to offer both an oriented input and better access to the focal region to accommodate the sensor design within a 2-D format. In such a design one of the collectors in FIG. 12 (e.g., 1202) would be removed entirely. In other applications two or more collectors 1201/1202 would be retained as in FIG. 12, and they would share a single sensor so as to permit more frequent sampling or to be optimized for multiple analytes. In addition, although the heater/absorber wires in the embodiment illustrated in FIG. 12 are semicircular, one skilled in the art will readily appreciate that the set of concentric heater/absorber wires in such an embodiment can also be non-circular, e.g., elliptical or rectangular, and all such configurations are within the scope of the present invention.

A second type of 2-D design is illustrated in FIG. 13. In the embodiment shown in FIG. 13, two molecular concentrators 1301 and 1302 having a concentric ring configuration as in FIG. 12 can be situated so that they face each other with their respective absorber/heater wires 1301*a*/1301*b* and 1302*a*/1302*b* (shown in cross-section) being interleaved with one another. Such a configuration can have more active surfaces and decreased distance between wires than in other configurations, and so can provide better analyte confinement and higher molecular transfer/delivery efficiency. In addition, in some embodiments, the two sets of wires in concentrators 1301 and 1302 can be functionalized differently for more selective control over multiple chemical species.

As noted above, other 2-D embodiments of heater wires, such as an arrangement of linearly offset wires or wires arranged in a ladder-like configuration, or combinations of arrangements of heater wires, can also be used in a molecular concentrator in accordance with the present invention, and all embodiments are deemed to be within the scope of the present disclosure.

3-D Designs:

If the 2-D collector/concentrator concepts described above are generalized to 3-D, such a change in geometry would in itself greatly enhance the concentrating power which would go as the cube of the size rather than as the square. In such an approach, it is important to be able to selectively deposit and functionalize the heater wire arrangements. Achieving a 3-D configuration of the heater/absorber wires using conventional multi-layer processes is feasible, though it will become increasingly difficult to accomplish as the number of wire levels grows beyond 10 or so. Recent progress in high-resolution 3-D printing/lithography will likely offer an attractive alternative, especially as the number of possible materials and the spatial resolution of these technologies continue to improve. See, e.g., the products and processes of Nanoscribe GmbH described at www.nanoscribe.de.

Figure 14:
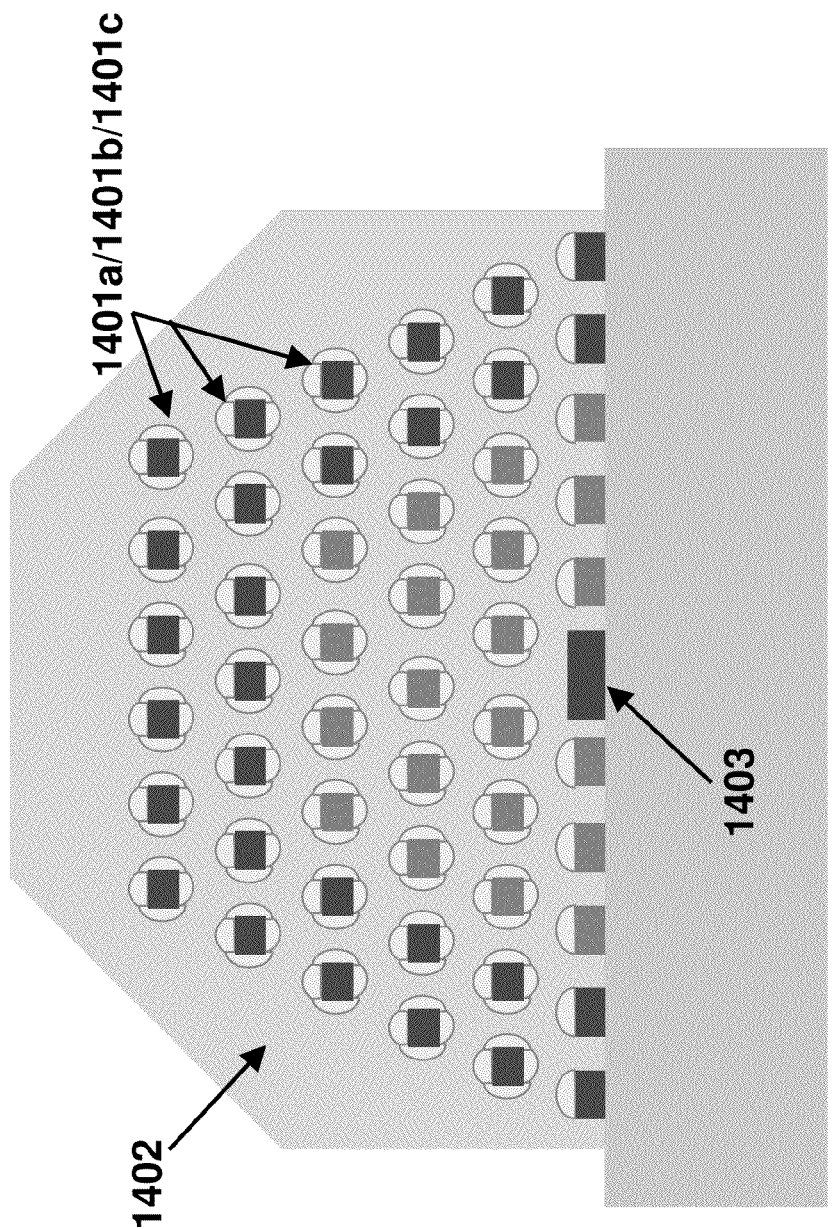
FIG. 14 is a block diagram illustrating aspects of another exemplary embodiment of a molecular concentrator based on thermal ratcheting in accordance with the present invention.

An exemplary embodiment of such a 3-D molecular collector/concentrator in accordance with the present invention is shown in FIG. 14. The design shown in FIG. 14 is essentially a 3-D generalization of the concentric ring design described above, though in this case not completely spherical in geometry so as to better provide mechanical support, access to the sensor, etc. Thus, as illustrated in FIG. 14, a molecular collector/concentrator in accordance with the present invention can comprise a three-dimensional arrangement of heater/absorber wires 1401*a*/1401*b*/1401*c*, etc. set into an inert support matrix 1402 and arranged around a sensor 1403. The molecules to be analyzed travel from one heater/absorber wire to another from the outer-most to the inner-most wires to be detected by the sensor in the manner described above with respect to the 2-D configurations.

In other embodiments (not shown), the heater/absorber wires can be arranged in a honeycomb configuration, though other three-dimensional geometries also may be utilized, and all such geometries are within the scope of the present disclosure.

Figure 15B:
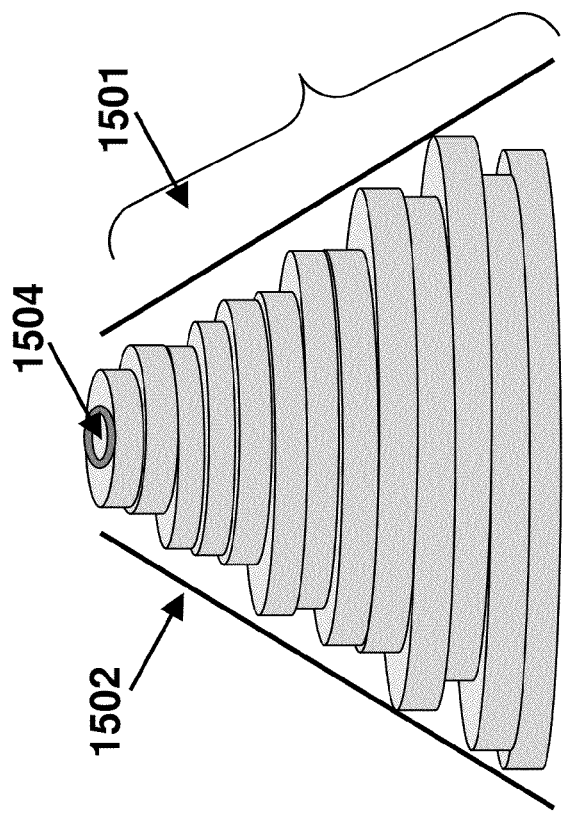
FIGS. 15A and 15B are block diagrams illustrating aspects of additional exemplary embodiments of a molecular concentrator based on thermal ratcheting in accordance with the present invention.
Figure 15A:
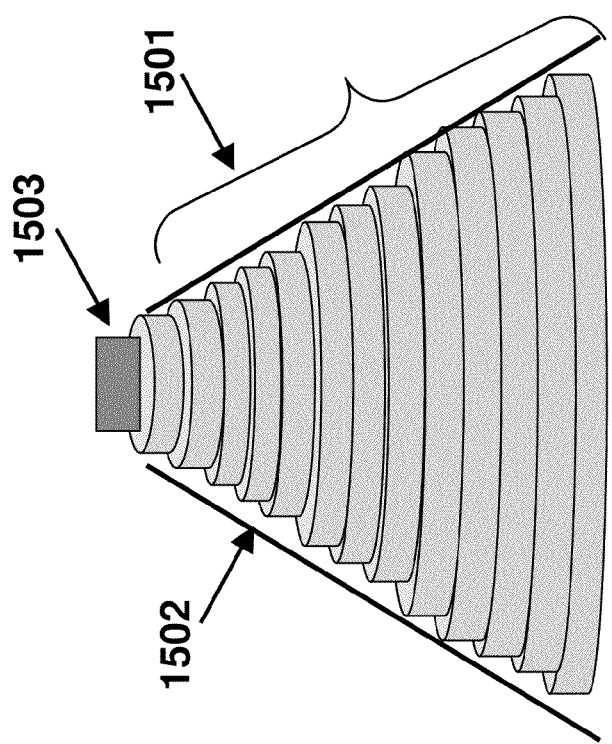

Another 3-D configuration, aspects of which are illustrated in FIG. 15A, can comprise a stacked series of heater/absorber wire rings forming a tapered cylinder or horn 1501 with a sensor 1503 situated at the apex of the cylinder. The stacked series of rings is surrounded by a non-absorbing layer 1502 closely covering the stacked structure, where the cover is configured to direct molecules desorbed from a first heater structure to a second heater structure in a predetermined manner. Similarly, as illustrated in FIG. 15B, the cylinder 1501, also surrounded by layer 1502, could be lined, with an open apex 1504 to allow air to escape, and the rings slightly offset so as to focus the target analyte away from the apex. The rings can be functionalized as described earlier. This configuration lends itself to performance on moving structures, for example, where the ambient already has some velocity relative to the sensor. It could be further modified so as to have a "grating" cover, providing an initial concentration gradient upon heating and desorption.

Few-Molecule Collectors:

In the foregoing designs the basic idea is to push trace vapor molecules into a small space in order to raise the concentration in the vicinity of the sensor and thereby lower the minimum detectable ambient level. Another use of the thermal ratcheting principle of the present invention would be to enable molecular delivery to nanosensors that are capable of responding to small numbers of molecules, e.g., see the nanofinger MIME sensor discussed in A. W. Snow, F. K. Perkins, M. G. Ancona, J. T. Robinson, E. S. Snow and E. E. Foos, "Disordered nanomaterials for chemielectric vapor sensing," *IEEE Sensors J.* 15, 1301 (2015), the entirety of which is incorporated by reference into the present disclosure.

Figure 16:
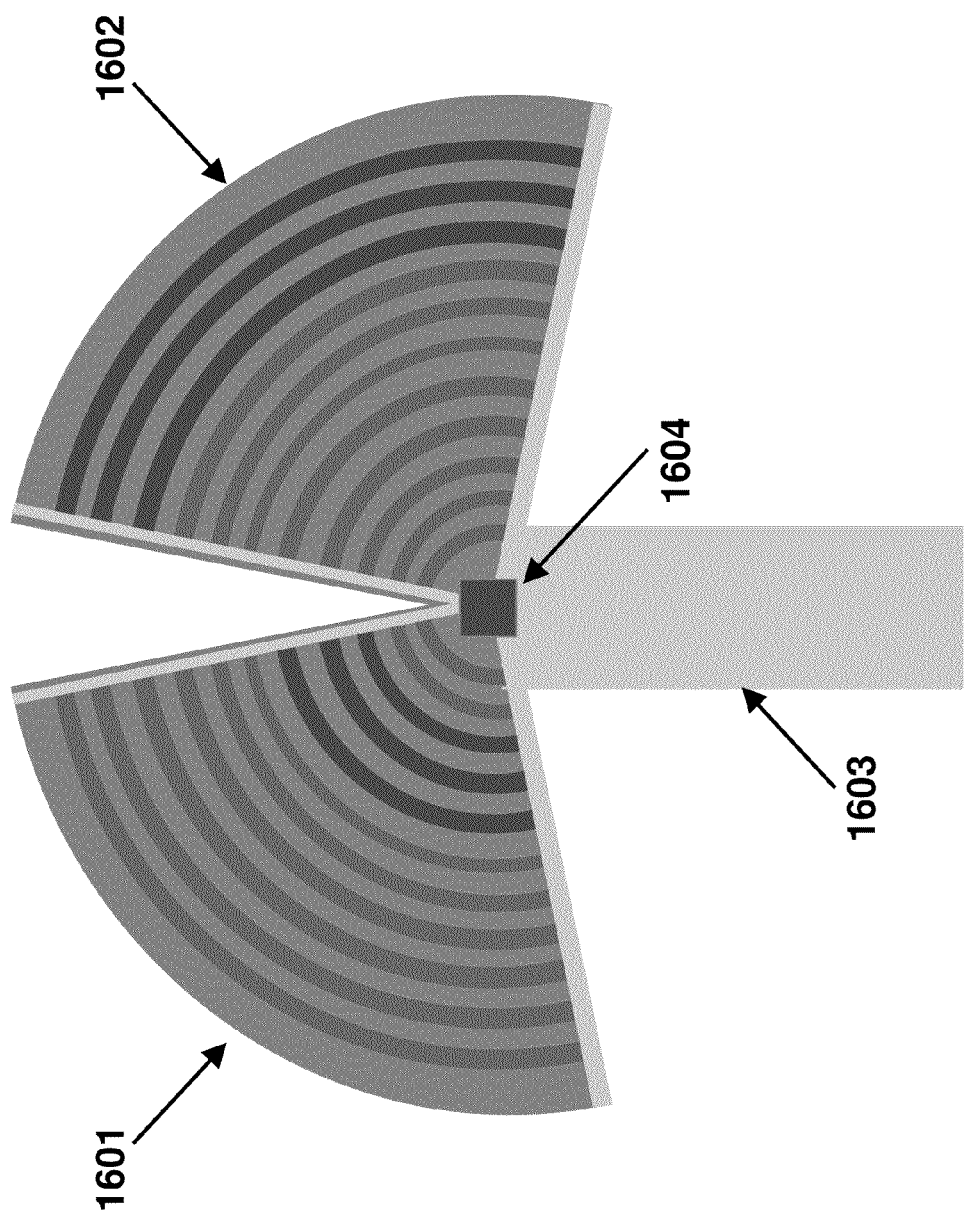
FIG. 16 is a block diagram illustrating aspects of another exemplary embodiment of a molecular concentrator based on thermal ratcheting in accordance with the present invention.

FIG. 16 illustrates an exemplary embodiment of a molecular concentrator in accordance with these aspects of the present invention. In the embodiment shown in FIG. 16, two thermal ratchet concentrators 1601 and 1602 in accordance with the present invention are arranged opposite one another around a central axis 1603 in a configuration reminiscent of moth antennae, with a sensor 1604 situated between them along the central axis. A molecular sensor having such a configuration enables the provision of directional information for following a very faint molecular vapor trail using, for example, a UAV. The movement of the molecules along the two concentrators are either in phase or out-of-phase. If out-of-phase, the different phasing of the two thermal ratchets allows a single sensor to distinguish the directions.

Figure 17:
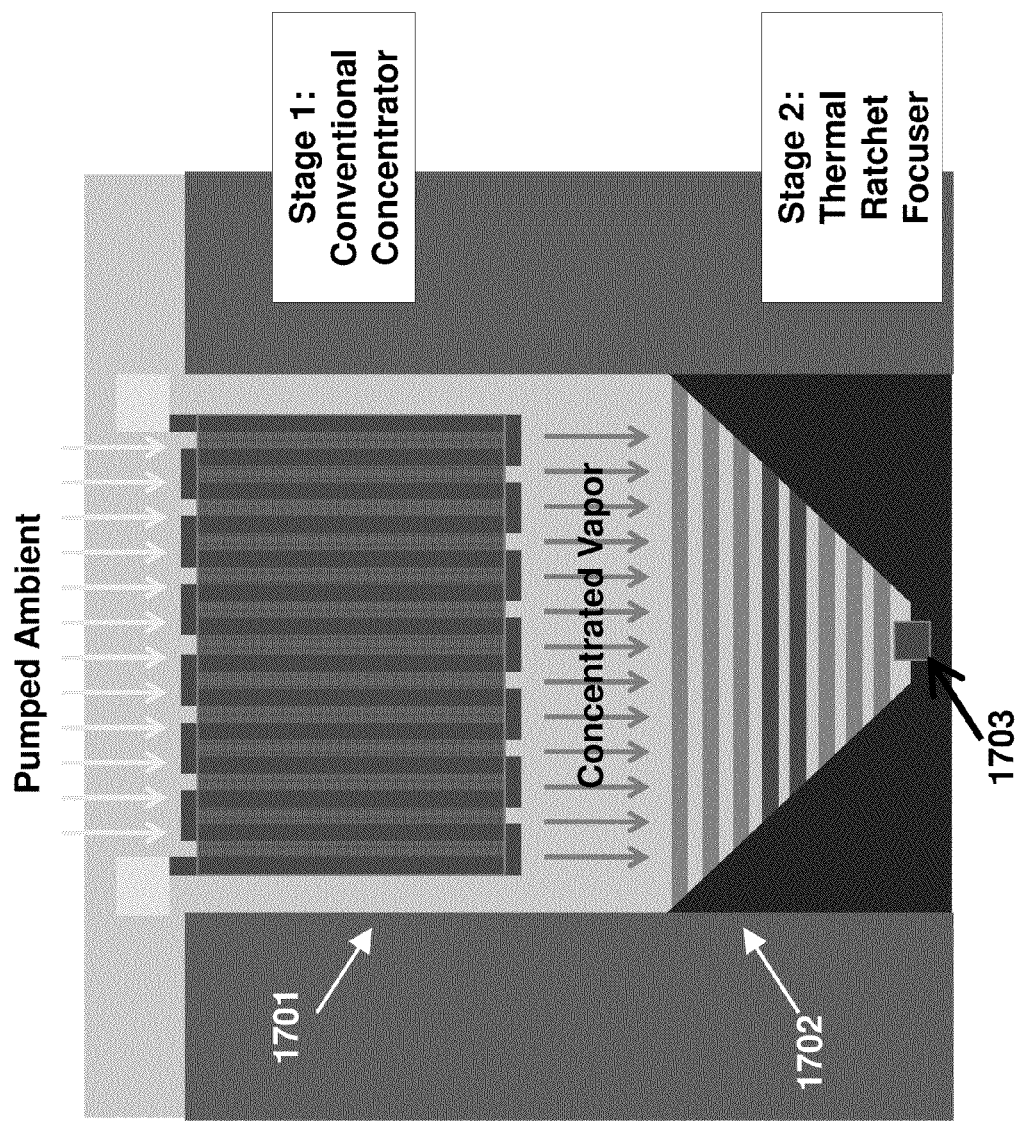
FIG. 17 is a block diagram illustrating aspects of another exemplary embodiment of a molecular concentrator based on thermal ratcheting in accordance with the present invention.

Hybrid Collectors:

Another category of thermal ratcheting molecular concentrators in accordance with the present invention is a two-stage molecular concentrator in which a conventional collector employing a carrier gas is combined with a thermal ratchet design. An exemplary embodiment of such an arrangement of this type is shown in FIG. 17. In the embodiment shown in FIG. 17, a conventional collector 1701 receives an input stream of pumped ambient to produce a concentrated vapor which is then fed into a thermal ratchet concentrator/focuser 1702 in accordance with the present invention that in turn delivers vapor molecules to a nanosensor 1703.

Advantages and New Features

The advantages and new features of the method and apparatus of the present invention over existing approaches may be summarized as follows:

The molecular collector/concentrator of the present invention exploits a novel thermal ratchet mechanism to concentrate and deliver trace vapor molecules to a chemical sensor for ultra-sensitive detection. The ratchet mechanism is instituted by heating a set of vapor-absorbing wires in proper sequence in order to drive the molecules in the direction perpendicular to the wires. It should be emphasized that this motion occurs without the carrier gas that is required by conventional pre-concentrator technologies and by gas chromatography, a fact that both improves the collection capability and simplifies the system (since neither a supply of a clean carrier gas nor an accompanying pump, valve system, or power supply is needed).

The present invention overcomes the diffusion limits that inflate the concentrations and times required for conventional point sensing systems to perform at the sub-part-per-billion concentration levels of interest (e.g., for vapor sensing of explosives).

The present invention enables nanosensors (with potential advantages for few-molecule sensitivity, selectivity, power consumption, etc.) to be used at low concentrations without prohibitively long collection times.

The present invention provides a new method (based on time, temperature, and molecular kinetics) for selectivity enhancement in point sensing.

The present invention eliminates the need for a sampling carrier gas or its supporting components (storage reservoir or air purification scrubber, pumping and valve system and associated power requirement).

The present invention eliminates the need for a conventional pre-concentrator and/or micro-gas chromatograph.

The present invention can provide rapid operation even at low analyte concentrations.

An apparatus in accordance with the present invention can be fabricated using simple planar lithographic fabrication.

The present invention is adaptable to a wireless distributed network system.

An apparatus in accordance with the present invention can be implemented in a miniature size adaptable for garment and small vehicle attachments, and for handheld and autonomous applications.

An apparatus in accordance with the present invention has lower power requirements than other miniaturized detection systems with similar performance.

Although particular embodiments, aspects, and features have been described and illustrated, it should be noted that the invention described herein is not limited to only those embodiments, aspects, and features, and it should be readily appreciated that modifications may be made by persons skilled in the art.

The present application contemplates any and all modifications within the spirit and scope of the underlying invention described and claimed herein, and all such embodiments are within the scope and spirit of the present disclosure.

What is claimed is:

1. An apparatus for directing vapor molecules to a desired location, comprising:

at least one two-dimensional arrangement of heater structures coupled to a selectively controllable source of heat energy configured to selectively apply heat energy to the heater structures, each of the heater structures having a low thermal mass and being configured to rapidly heat upon an application of the heat energy and to rapidly cool in the absence of the heat energy, each of the heater structures being thermally isolated one from another so that a heating or a cooling of one structure does not heat or cool a neighboring structure or arrangement of heater structures;

wherein each of the heater structures is configured to sorb molecules from a vapor incident on the structures when the structure is cool and to desorb at least some of the sorbed molecules when the structure is heated such that at least some of the desorbed molecules are then sorbed by a neighboring unheated structure; and wherein the source of heat energy is configured to selectively apply and remove heat energy to one or more of the heater structures in a predefined sequence, the heated and cooled heater structures comprising a thermal ratchet in which molecules from the vapor selectively sorb, desorb, and diffuse from one heater structure to another to produce a two-dimensional, converging transport of the molecules to the desired location at an elevated concentration of the desorbed analyte.

2. The apparatus according to claim 1, wherein each of the two-dimensional arrangements of heater structures comprises a two-dimensional arrangement of a plurality of thermally isolated metal wires, each of the wires being coupled to the source of the heat energy such that the heat energy can be selectively applied and removed from each individual wire.

3. The apparatus according to claim 1, comprising a plurality of two-dimensional arrangements of heater structures, each of the arrangements of heater structures being independent from any other arrangement of heater structures and having a separately controllable sequence of heating and cooling to cause molecules from the vapor to selectively sorb, desorb, and diffuse from one heater structure to an adjacent heater structure to produce the two-dimensional, converging transport of the molecules to the desired location at an elevated concentration.

4. The apparatus according to claim 3, wherein at least one of the plurality of two-dimensional arrangements of heater structures is configured to selectively sorb and desorb a different molecule than at least one other of the plurality of two-dimensional arrangements of heater structures.

5. The apparatus according to claim 1, wherein the apparatus comprises a plurality of concentric arrangements of thermally isolated heater structures, each of the heater structures being coupled to the source of heat energy such that the heat energy can be selectively applied and removed from each individual heater structure;
   wherein the heat energy is selectively applied and removed from one or more of the heater structures to produce a two-dimensional, converging transport of the desorbed molecules from the vapor to move from heater structures located at a periphery of the concentric arrangement to heater structures near the center of the concentric arrangement.

6. The apparatus according to claim 1, wherein the apparatus comprises at least one non-concentric arrangement of thermally isolated heater structures, each of the heater structures being coupled to the source of heat energy such that the heat energy can be selectively applied and removed from each individual heater structure;
   wherein the heat energy is selectively applied and removed from one or more of the heater structures to produce a two-dimensional, converging transport of the desorbed molecules from heater structures located at a first location in the arrangement of heater structures to heater structures located at a second location in the arrangement of heater structures to obtain an elevated concentration of sorbed analyte.

7. The apparatus according to claim 1, wherein the apparatus comprises a first set of heater structures in a first two-dimensional arrangement and a second set of heater structures in a second two-dimensional arrangement;
   wherein the heat energy is selectively applied and removed from one or more of the heater structures in each the first and second sets of heater structures to produce a two-dimensional, converging transport of the molecules from heater structures located at a periphery of the first and second two-dimensional arrangements to the desired location.

8. The apparatus according to claim 7, wherein the first and the second two-dimensional arrangements of heater structures are configured to cause the movement of molecules from the heater structures in the first set of heater structures to the desired location to be in temporal phase with the movement of molecules from the heater structures in the second set of heater structures.

9. The apparatus according to claim 7, wherein the first and the second two-dimensional arrangements of heater structures are configured to cause the movement of molecules from the heater structures in the first set of heater structures to the desired location to be out of temporal phase with the movement of molecules from the heater structures in the second set of heater structures.

10. The apparatus according to claim 1, further comprising a source of cooling energy coupled to at least one of the arrangements of heater structures;
    wherein the heater structures are heated upon application of the heat energy and are cooled to below room temperature upon an application of the cooling energy.

11. The apparatus according to claim 1 wherein the heater structures have a surface treatment comprising an alteration in the surface composition of the heater structures, the surface treatment being configured to adsorb molecules from the vapor when the structure is cool and to desorb some of the adsorbed molecules when the structure is heated.

12. The apparatus according to claim 1, wherein the heater structures have a coating thereon, the coating comprising an absorptive material configured to absorb molecules from the vapor when the structure is cool and to desorb at least some of the sorbed molecules when the structure is heated.

13. The apparatus according to claim 12, wherein the coating is configured to selectively desorb specified analyte molecules so that a vapor that reaches the desired location has an enhanced concentration of the specified analyte molecules.

14. The apparatus according to claim 12, wherein the coating is configured to selectively retain specified analyte molecules when the heat-conducting material is cooled so that a vapor that reaches the desired location has a reduced concentration of the specified analyte molecules.

15. The apparatus according to claim 12, wherein at least one of the coating and the heat energy is configured to selectively produce a desired concentration of a desired analyte molecule in the vapor that diffuses to the desired location.

16. The apparatus according to claim 12, wherein the coating is configured to have an affinity and sorbtion-desorbption temperature behavior appropriate for the selective direction of amine vapors to the desired location.

17. The apparatus according to claim 1, wherein the desired location is a specified heater structure proximate to a sensor configured to receive and analyze at least one analyte molecule in the vapor;
    wherein when the specified heater structure is heated, analyte molecules sorbed on the specified heater structure are desorbed from the specified heater structure and are received by the sensor.

18. The apparatus according to claim 1, wherein the apparatus is a sensing apparatus and further comprises a sensor chip comprising at least one sensor configured to receive and analyze at least one analyte in the vapor composition;
    wherein when the molecules from the vapor reach a specified heater structure, heat energy is applied to the specified heater structure to cause the specified heater structure to become heated; and
    wherein analyte molecules desorb from the heated heater structure and are detected by the sensor.

19. The apparatus according to claim 1, wherein the at least one two-dimensional arrangement of heater structures is suspended over the substrate.

20. The apparatus according to claim 1, wherein the transport of the molecules proceeds solely by means of thermal ratcheting of the molecules from one heater structure to another without the aid of a carrier gas.

21. An apparatus for directing vapor molecules to a desired location, comprising:
    a first set of heater structures in a first two-dimensional arrangement and a second set of heater structures in a second two-dimensional arrangement, the first and second sets of heater structures facing one another so that the first set heater structures are interleaved with the second set of heater structures, each of the heater structures having a low thermal mass and being coupled to a corresponding selectively controllable source of heat energy configured to selectively apply heat energy to the heater structures, the first and second set of heater structures, each of the heater structures being further configured to rapidly heat upon an application of the heat energy and to rapidly cool in the absence of the heat energy, each of the heater structures further being thermally isolated one from another so that a heating or a cooling of one structure does not heat or cool a neighboring structure or arrangement of heater structures;

wherein each of the heater structures is configured to sorb molecules from a vapor incident on the structures when the structure is cool and to desorb at least some of the sorbed molecules when the structure is heated, at least some of the desorbed molecules then being sorbed by a neighboring unheated structure;

wherein the source of heat energy is configured to selectively apply and remove heat energy to one or more of the heater structures in a predefined sequence, the heated and cooled heater structures comprising a thermal ratchet in which molecules from the vapor selectively sorb and desorb and diffuse from one heater structure to another to produce a two-dimensional, converging transport of the molecules to the desired location at an elevated concentration of the desorbed analyte.

22. An apparatus for directing vapor molecules to a desired location, comprising:

at least one two-dimensional arrangement of heater structures coupled to a selectively controllable source of heat energy configured to selectively apply heat energy to the heater structures, each of the heater structures having a low thermal mass and being configured to rapidly heat upon an application of the heat energy and to rapidly cool in the absence of the heat energy, each of the heater structures being thermally isolated one from another so that a heating or a cooling of one structure does not heat or cool a neighboring structure or arrangement of heater structures; and further comprising at least one three-dimensional arrangement of heater structures, each of the three-dimensional arrangement of heater structures being thermally isolated from any other arrangement of heater structures and having a separately controllable sequence of heating and cooling;

wherein each of the heater structures is configured to sorb molecules from a vapor incident on the structures when the structure is cool and to desorb at least some of the sorbed molecules when the structure is heated, at least some of the desorbed molecules then being sorbed by a neighboring unheated structure; and wherein the source of heat energy is configured to selectively apply and remove heat energy to one or more of the heater structures in a predefined sequence, the heated and cooled heater structures comprising a thermal ratchet in which molecules from the vapor selectively sorb and desorb and diffuse from one heater structure to another to produce a two-dimensional, converging transport of the molecules to the desired location at an elevated concentration of the desorbed analyte.

23. An apparatus for directing vapor molecules to a desired location, comprising:

at least one three-dimensional arrangement of heater structures coupled to a selectively controllable source of heat energy configured to selectively apply heat energy to the heater structures, each of the heater structures having a low thermal mass and being configured to rapidly heat upon an application of the heat energy and to rapidly cool in the absence of the heat energy, each of the heater structures being thermally isolated one from another so that a heating or a cooling of one structure does not heat or cool a neighboring structure;

wherein each of the heater structures is configured to sorb molecules from a vapor incident on the structures when the structure is cool and to desorb at least some of the sorbed molecules when the structure is heated, at least some of the desorbed molecules then being sorbed by a neighboring structure; and wherein the heat energy is selectively applied and removed from one or more of the heater structures in a predefined sequence to cause the molecules from the vapor to selectively sorb and desorb from one heater structure to another at the desired location in a desired manner.

24. The apparatus according to claim 23, comprising a plurality of heater structures arranged in a three-dimensional honeycomb arrangement within an inert medium.

25. The apparatus according to claim 23, comprising a plurality of concentric ring heater structures arranged in a three-dimensional matrix within an inert medium.

26. The apparatus according to claim 23, comprising a plurality of heater structures arranged in a stacked arrangement and further comprising a closely spaced and non-absorbing layer covering the stacked structure, the cover being configured to direct molecules desorbed from a first heater structure to a second heater structure in a predetermined manner.

27. The apparatus according to claim 26, further comprising a sensor situated at an apex of the stacked arrangement of heater structures.

28. The apparatus according to claim 23, comprising a plurality of three-dimensional arrangements of heater structures configured to cause the movement of molecules from the heater structures in a first set of heater structures to the desired location to be in temporal phase with the movement of molecules from the heater structures in a second set of heater structures.

29. The apparatus according to claim 23, comprising a plurality of three-dimensional arrangements of heater structures configured to cause the movement of molecules from the heater structures in a first set of heater structures to the desired location to be out of temporal phase with the movement of molecules from the heater structures in a second set of heater structures.

30. The apparatus according to claim 23, wherein the apparatus is a sensing apparatus and further comprises a sensor chip comprising at least one sensor configured to receive and analyze at least one analyte in the vapor composition;

wherein when the molecules from the vapor reach a specified heater structure, heat energy is applied to the specified heater structure to cause the specified heater structure to become heated; and wherein analyte molecules desorb from the heated heater structure and are adsorbed by the sensor.

31. The apparatus according to claim 23, wherein the apparatus comprises a first set of heater structures in a first three-dimensional arrangement and a second set of heater structures in a second three-dimensional arrangement;

wherein the heat energy is selectively applied and removed from one or more of the heater structures in each the first and second sets of heater structures to cause the molecules from the vapor to move from heater structures located at a periphery of the first and second non-coplanar arrangements to a desired location located at the central axis.

32. The apparatus according to claim 23, wherein the apparatus comprises a first set of heater structures in a three-dimensional arrangement and a second set of heater structures in a two-dimensional arrangement;

wherein the heat energy is selectively applied and removed from one or more of the heater structures in each the first and second sets of heater structures to cause the molecules from the vapor to move from heater structures located at a periphery of the first and second non-coplanar arrangements to a desired location located at the central axis.

33. An apparatus for directing vapor molecules to a desired location, comprising:

a collector configured to collect molecules from a vapor incident on the apparatus and to concentrate the collected molecules to produce a concentrated analyte;

at least one arrangement of heater structures configured to receive the concentrated analyte from the collector, the heater structures being coupled to a selectively controllable source of heat energy configured to selectively apply heat energy to the heater structures, each of the heater structures having a low thermal mass and being configured to rapidly heat upon an application of the heat energy and to rapidly cool in the absence of the heat energy, each of the heater structures and each of the arrangements of heater structures being thermally isolated one from another so that a heating or a cooling of one structure does not heat or cool a neighboring structure or arrangement of heater structures;

wherein each of the heater structures is configured to sorb molecules from the concentrated analyte when the structure is cool and to desorb at least some of the sorbed molecules when the structure is heated such that at least some of the desorbed molecules are then sorbed by a neighboring unheated structure; and wherein the source of heat energy is configured to selectively apply and remove heat energy to one or more of the heater structures in a predefined sequence, the heated and cooled heater structures comprising a thermal ratchet in which molecules from the concentrated analyte selectively sorb and desorb and diffuse from one heater structure to another to produce a two-dimensional, converging transport of the molecules to the desired location at an elevated concentration of the desorbed analyte.

34. The apparatus according to claim 33, wherein the apparatus is a sensing apparatus and further comprises a sensor chip comprising at least one sensor configured to receive and analyze at least one molecule from the vapor incident on the collector;

wherein when the molecules from the concentrated vapor reach a specified heater structure, heat energy is removed from the specified heater structure to cause the specified heater structure to cool; and wherein analyte molecules desorb from the cooled heater structure and are adsorbed by the sensor.

35. The apparatus according to claim 33, wherein the at least one two-dimensional arrangement of heater structures is suspended over the substrate.

* * * * *